(12) United States Patent
Chase et al.

(10) Patent No.: US 12,076,295 B2
(45) Date of Patent: Sep. 3, 2024

(54) TRUNK AND LEG COMPRESSION GARMENT SYSTEMS

(71) Applicant: TACTILE SYSTEMS TECHNOLOGY, INC., Minneapolis, MN (US)

(72) Inventors: Daniel G. Chase, Menomonie, WI (US); Kristian Dior Gamble, Minneapolis, MN (US); Mark R. Riley, St. Paul, MN (US); Wade Andrew Zander, Minneapolis, MN (US)

(73) Assignee: TACTILE SYSTEMS TECHNOLOGY, INC., Minneapolis, MN (US)

( * ) Notice: Subject to any disclaimer, the term of this patent is extended or adjusted under 35 U.S.C. 154(b) by 1153 days.

(21) Appl. No.: 16/182,162

(22) Filed: Nov. 6, 2018

(65) Prior Publication Data
US 2019/0133871 A1  May 9, 2019

Related U.S. Application Data

(60) Provisional application No. 62/582,121, filed on Nov. 6, 2017.

(51) Int. Cl.
*A61H 9/00* (2006.01)
*A41D 13/00* (2006.01)
(Continued)

(52) U.S. Cl.
CPC ....... *A61H 9/0078* (2013.01); *A41D 13/0015* (2013.01); *A61F 13/0273* (2013.01);
(Continued)

(58) Field of Classification Search
CPC .......... A61H 9/0078; A61H 2201/1621; A61H 2201/1409; A61H 2201/1238;
(Continued)

(56) References Cited

U.S. PATENT DOCUMENTS 2,361,242 A * 10/1944 Rosett ................. A61H 9/0078
601/152
3,116,735 A  1/1964 Geimer
(Continued)

FOREIGN PATENT DOCUMENTS

| CN | 2461321 Y | 11/2001 | |
|---|---|---|---|
| WO | WO 03/041621 A1 | 5/2003 | |
| WO | WO-2015200203 A1 * | 12/2015 | ........... A61F 13/062 |

OTHER PUBLICATIONS

University, R., & OpenStaxCollege. (Mar. 6, 2013). Bones of the lower limb. Anatomy Physiology. Retrieved Oct. 14, 2022. (Year: 2013).*

(Continued)

*Primary Examiner* — Tu A Vo
*Assistant Examiner* — Kelsey E Baller
(74) *Attorney, Agent, or Firm* — Mueting Raasch Group

(57) ABSTRACT

Compression garment systems may include a trunk garment and a leg garment to be positioned about a trunk and leg of a body to provide compression therapy thereto. The trunk garment and the garment may include a plurality of controllable pressure applying regions to move lymph from the leg and trunk.

30 Claims, 19 Drawing Sheets

(51) Int. Cl.
*A61F 13/02* (2024.01)
*A61F 13/06* (2006.01)
*A61F 13/08* (2006.01)
*A61F 13/14* (2006.01)

(52) U.S. Cl.
CPC .............. *A61F 13/06* (2013.01); *A61F 13/08* (2013.01); *A61F 13/085* (2013.01); *A61F 13/148* (2013.01); *A41D 2400/322* (2013.01); *A41D 2400/44* (2013.01); *A61H 2201/0192* (2013.01); *A61H 2201/1238* (2013.01); *A61H 2201/1409* (2013.01); *A61H 2201/1621* (2013.01); *A61H 2201/1642* (2013.01); *A61H 2201/1645* (2013.01); *A61H 2201/165* (2013.01); *A61H 2201/5056* (2013.01); *A61H 2205/081* (2013.01); *A61H 2205/10* (2013.01); *A61H 2209/00* (2013.01)

(58) Field of Classification Search
CPC ...... A61H 2201/1645; A61H 2201/165; A61H 2201/5056; A61H 2205/081; A61H 2205/10; A61H 2209/00; A61F 13/06; A61F 13/02; A61F 13/0273; A61F 13/085; A41D 13/0015; A41D 17/00; A41D 17/005; A41D 2400/322; A41D 2400/44; A41D 2200/10; A41F 9/00; A41F 9/005

See application file for complete search history.

(56) References Cited

U.S. PATENT DOCUMENTS

| | | | |
|---|---|---|---|
| 3,288,132 A * | 11/1966 | Meredith | A61H 9/0078 601/152 |
| 3,659,593 A | 5/1972 | Vail | |
| 4,355,632 A | 10/1982 | Sandman | |
| 4,577,622 A | 3/1986 | Jennings | |
| 5,496,262 A * | 3/1996 | Johnson, Jr. | A61H 9/0078 128/DIG. 20 |
| D381,428 S | 7/1997 | Torok et al. | |
| 5,782,790 A | 7/1998 | Allen | |
| 5,938,628 A * | 8/1999 | Oguri | A61H 9/0078 601/150 |
| 6,179,796 B1 | 1/2001 | Waldridge | |
| 6,224,538 B1 * | 5/2001 | Wang | A61H 9/0078 600/19 |
| 6,338,723 B1 * | 1/2002 | Carpenter | A61F 13/085 602/62 |
| D472,640 S | 4/2003 | Crowe et al. | |
| 6,645,165 B2 | 11/2003 | Waldridge et al. | |
| D499,806 S | 12/2004 | Machin et al. | |
| 6,860,862 B2 | 3/2005 | Waldridge et al. | |
| 6,966,884 B2 | 11/2005 | Waldridge et al. | |
| 7,025,737 B2 | 4/2006 | Modglin | |
| 7,044,924 B1 * | 5/2006 | Roth | A61H 9/0078 601/151 |
| 7,048,702 B2 | 5/2006 | Hui | |
| D612,059 S | 3/2010 | Haney et al. | |
| 7,947,003 B2 | 5/2011 | Bonnefin et al. | |
| 8,522,364 B2 * | 9/2013 | O'Brien | A41F 9/00 2/227 |
| 8,622,943 B2 * | 1/2014 | Ben-Nun | A61H 9/0078 601/149 |
| D728,111 S | 4/2015 | Walmsley | |
| 8,998,835 B2 | 4/2015 | McVicker | |
| 9,027,408 B2 | 5/2015 | Toth et al. | |
| 9,314,363 B2 | 4/2016 | Ingimundarson et al. | |
| 9,320,634 B2 | 4/2016 | Paulos | |
| D759,827 S | 6/2016 | Greinwalder et al. | |
| 9,398,972 B2 | 7/2016 | Yip et al. | |
| D783,937 S | 4/2017 | Miller et al. | |
| 10,010,744 B2 | 7/2018 | Sekula et al. | |
| 10,076,462 B2 | 9/2018 | Johnson et al. | |
| D834,208 S | 11/2018 | Wennen et al. | |
| 10,159,592 B2 | 12/2018 | Ingimundarson et al. | |
| D848,625 S | 5/2019 | Chase et al. | |
| D849,254 S | 5/2019 | Chase et al. | |
| 2001/0018563 A1 * | 8/2001 | Waldridge | A61H 9/0078 601/152 |
| 2002/0099409 A1 * | 7/2002 | Hui | A61H 9/0078 606/201 |
| 2003/0167557 A1 | 9/2003 | LaShoto et al. | |
| 2004/0054306 A1 | 3/2004 | Roth et al. | |
| 2005/0143683 A1 * | 6/2005 | Waldridge | A61H 9/0078 601/151 |
| 2005/0154336 A1 | 7/2005 | Kloecker et al. | |
| 2006/0004245 A1 * | 1/2006 | Pickett | A61H 31/008 600/16 |
| 2006/0117598 A1 * | 6/2006 | Czaplewski | A43B 3/163 36/2 R |
| 2009/0076432 A1 * | 3/2009 | Winkler | A61F 13/08 602/76 |
| 2014/0107546 A1 * | 4/2014 | Falconio-West | A61F 13/08 601/151 |
| 2014/0194796 A1 * | 7/2014 | Noskowicz | A61H 9/0092 601/151 |
| 2014/0259555 A1 * | 9/2014 | Horn | A44B 99/00 24/306 |
| 2016/0242984 A1 * | 8/2016 | Takagi | A61H 9/0078 |
| 2017/0258672 A1 * | 9/2017 | Wennen | A61H 1/008 |

OTHER PUBLICATIONS

International Patent Application No. PCT/US2018/059421, filed Nov. 6, 2018; International Search Report / Written Opinion issued Jan. 28, 2019; 14 pages.

* cited by examiner

TRUNK AND LEG COMPRESSION GARMENT SYSTEMS

CROSS-REFERENCE TO RELATED APPLICATIONS

This application claims the benefit of U.S. Provisional Application No. 62/582,121, filed Nov. 6, 2017, and entitled "Trunk and Leg Compression Garment Systems," which is incorporated herein in its entirety.

FIELD OF THE DISCLOSURE

The present disclosure relates generally to compression garment systems including trunk and leg compression garments and to methods for applying pressure to one or more trunk and leg portions of the body using such garments and systems.

BACKGROUND

Various types of compression garments are available, for example, such as for treatment of lymphedema, edema, wound healing, etc. For example, garments may include inflatable chambers or cells (or other actuatable elements) to provide compression therapy to patients and may be positioned about any body portion of a person or animal. Specifically, the garments may be positioned about body portions that exhibit swelling due to a build-up of lymph and/or other fluid and that would benefit from compression therapy provided by the garments. For example, such chambers or cells may be inflatable to one or more different pressures in a variety of sequences to provide the therapy to the patient by moving lymph from one body region to another. In other words, such compression garments may be placed around at least a portion of an individual's body for use in applying pressure to the body at one or more body regions (such as, e.g., an affected extremity). These compression garments may be donned (e.g., put on) and doffed (e.g., taken off or removed) by patients themselves or with help from others.

SUMMARY

Exemplary compression systems may include a trunk garment and a leg garment that may be used separately or in conjunction with each other to, e.g., provide compression therapy to a user's body. Each of the trunk and leg garments may include a plurality of pressure applying regions to apply compression therapy to corresponding regions of the user's body. The pressure applying regions may define chambers configured to receive fluid to inflate or deflate to expand or contract the chambers in size to provide the compression therapy to the user's body.

The trunk garment may be configured to be positioned, or may be positionable, about the user's trunk to provide compression therapy to the at least a portion of the user's trunk and at least an upper region of both of the user's legs, e.g., located proximate the user's thighs. In other words, the exemplary trunk garment may provide bilateral thigh coverage, which may allow for treatment of both legs simultaneously. In at least one embodiment, the trunk garment extends from a location proximate, or near, the user's waist to a thigh region, or location, proximate an upper portion of the user's thighs. The trunk garment may include three portions. The first portion, which may be referred to as a wraparound portion, may be donned about a waist region of the user's body, and the second and third portions may be donned about the user's left and right legs, respectively. The trunk garment may include one or more loop portions (e.g., strapping, webbing, etc.) extending from various regions or portions of the trunk garment that are configured to be grasped by a user to don the trunk garment and to remove the trunk garment from the user's body. For example, the loop portions may be coupled to and extend from regions of the trunk garment configured be located proximate the user's waist when donned and/or regions of the trunk garment configured be located proximate the user's thighs when donned. In other words, the exemplary trunk garment may include a webbing belt around waist that may allow patients to grab onto the belt to pull on the garment and other loops, webbing, or straps about other portions to assist patients in donning and doffing the garment.

Tubing may be coupled to the trunk garment to provide, or transport, fluid such as, e.g., air, to one or more pressure applying regions of the trunk garment. The tubing may extend from a region of the trunk garment between an upper end region and a bottom end region of the trunk garment (e.g., as opposed to extending from the top end region or from the bottom end region). In other words, the tubing may extend from a middle region of the trunk garment that is not considered to be an upper or lower end of the garment. Further, the tubing may be described as extending from a side region, or area, of the trunk garment. In other words, the exemplary trunk garment may include tubing that exits on side of garment, which may reduce interference of the tubes with either upper or lower extremity garments. Additionally, the exemplary garments described herein may include a strain relief portion that is configured to relieve any strain from the tubing that is part of, or runs about, the garment and is operably coupled to the pressure applying regions. The strain relief portion may be attached to an exterior surface of the remainder of the compression garment and may also be removably attached to the bundle of tubing extending away from the compression garment. When the tubing is pulled by, e.g., a user attaching the opposite end of the tubing to a pump controller, the force applied to the tubing will be directed to the strain relief portion as opposed to remainder of the tubing that extends to pressure applying regions of the garment. More specifically, the tubing may be coupled to each of the pressure applying regions on a proximal end and to a connector that is couplable to a pump controller on a distal end. When the distal end is pulled, the strain relief portion may relive the proximal end of the tubing from such force. Instead, the force from pulling on the distal end of the tubing may be transferred through the strain relief portion to the exterior surface of the garment.

The leg garment may be donned about one of the user's left or right legs and may extend from the user's upper leg, or thigh region, to another lower portion of the user's leg such as, e.g., the calf, the ankle, the foot, etc. The leg garment may include one or more loop portions (e.g., strapping, webbing, etc.) extending from various regions or portions of the leg garment that are configured to be used by a user to don the leg garment and to remove the leg garment from the user's body. For example, a loop portion may be located proximate a region of the leg garment that is configured to be located proximate, or near, the user's heel or ankle when the leg garment is donned, and this loop portion may be used by the user to remove the leg garment from the user's leg by, e.g., placing a portion of the user's opposing foot (e.g., heel, toes, etc.) into the loop portion to maintain the position of the leg garment while pulling the leg out of the leg garment and/or to push the leg garment off the leg about which the leg garment is donned. This loop portion may be referred to as a "stomp" strap. In other words, webbing on the back of the heel of the garment may give, or provide, a patient structure to a place their first foot to help pull their second foot out of the garment after treatment.

Further, for example, one or more loop portions may be located proximate and/or extending from a region of the leg garment near the upper leg region, or thigh region, of the user to allow a user to "pull on" the leg garment onto their leg. Still further, for example, one or more loop portions may be coupled to one or more leg straps configured to wrap around, or about, a portion of the user's leg to adjust the size of the leg garment about the user's leg, and such loop portions may be grasped by a user to adjust such leg straps. In other words, webbing loops on adjustment tabs or straps may be coupled to the leg garment that are, e.g., easy for a user to grab and then adjust the garment. Further, in one or more embodiments, the adjustment tabs or straps may be identified, e.g., using colors, alphanumeric indicators, etc. as a training aid for patients. The leg straps may be coupled to the leg garment via hook-and-loop fasteners. In one or more embodiments, the leg garment may further include replaceable, sacrificial hook-and-loop pads that removably attach, or couple, to the leg garment more aggressively than the leg straps. Thus, the leg straps may be removably attached, or coupled, to the replaceable, sacrificial hook-and-loop pads, which in turn, are removably attached, or coupled, to the leg garment. Since the leg straps are removed and reattached to the sacrificial hook-and-loop pads as opposed to the outer surface of the leg garment, such removal and reattachment may, e.g., reduce the wear on the outer surface of the leg garment.

The leg garment may further include a heel element extending between a calf portion and a foot portion that is configured to receive the heel of the leg of the user. It may be described that the foot portion is "form fitted" and wraps about a user's foot to provide compression therapy thereto. The heel element may be shaped and sized to allow fitment of the leg garment about the curvature of the calf to the foot of the leg about the tarsal region. Thus, the exemplary leg garment may be described as improving foot ergonomics as opposed to previous leg garments that were shaped like a straight tube extending along an axis that can cause users' feet to slip out of gaps around the foot and ankle portions of the leg garment. The exemplary leg garment may be described as eliminating such gaps and providing users a definitive heel cup to help them orient the foot in the leg garment.

The exemplary systems may further include a controller to control the plurality of pressure applying regions of the garments to apply pressure to a plurality of portions or regions of the user's body. The controller may be operably coupled to garments to control pressure applied by the plurality of pressure applying regions in at least a preparation phase and a drainage phase. When in the preparation phase, the controller may be configured to apply pressure to the plurality of portions of the trunk and leg of the user's body to prepare the body for lymph to be drained from the trunk and/or leg. When in the drainage phase, the controller may be configured to apply pressure to the plurality of portions of the trunk and/or leg using the plurality of pressure applying regions to move lymph at least from the leg and/or trunk towards one or more upper regions of trunk or torso.

One exemplary compression garment system may include, or comprise, a trunk garment and at least one leg garment. The trunk garment may be donned about a trunk of a user to apply compression to the trunk and at least a portion of both legs of the user. The trunk garment may include, or comprise, one or more trunk pressure applying regions controllable to apply pressure to a portion of the trunk and at least a portion of both legs of the user. The leg garment may be donned about a right or left leg of the user to apply compression to the leg. The leg garment may include, or comprises, one or more leg pressure applying regions controllable to apply pressure to at least a portion of the leg.

Another exemplary compression garment system may include, or comprise, a trunk garment to be donned about a trunk of a user to apply compression to the trunk and at least a portion of both legs of the user. The trunk garment may include, or comprise, one or more trunk pressure applying regions controllable to apply pressure to a portion of the trunk and at least a portion of both legs of the user. The one or more trunk pressure applying regions may be concentrically positioned about the trunk of the user such that each of the one or more trunk pressure applying regions substantially lies in a plane perpendicular to an axis extending substantially along the spine of the user.

In one or more embodiments, the trunk garment may define a right upper leg opening to receive at least portion of the femoral region of the right leg of the user and a left upper leg opening to receive at least portion of the femoral region of the left leg of the user. The trunk garment may apply compression to at least a portion of the femoral region of both of the right and left legs of the user.

In one or more embodiments, the trunk garment may extend from at least an upper end region locatable proximate the pelvic region of the user to at least a lower end region locatable proximate the femoral region of both of the right and left legs of the user. Further, the trunk garment may further include, or comprise, tubing operably coupled to the one or more trunk pressure applying regions to transmit fluid to the one or more trunk pressure applying regions, wherein the tubing extends from the trunk garment between the upper end region and the lower end region. Still further, the system may further include, or comprise, a strain relief portion removably coupled to the trunk garment and removably coupled to the tubing to relieve strain from the operably coupling between the one or more trunk pressure applying regions and the tubing.

In one or more embodiments, the trunk garment may further include, or comprise, one or more loop portions proximate the upper end region to be grasped by a user when donning the trunk garment to assist in donning the trunk garment. Further, in one or more embodiments, the one or more trunk pressure applying regions may be concentrically positioned about the trunk of the user such that each of the one or more trunk pressure applying regions substantially lies in a plane perpendicular to an axis extending substantially along the spine of the user.

In one or more embodiments, the trunk garment may further include, or comprise, a wraparound portion extending from a first anterior end region to a second anterior end region and configured to be wrapped about the user's trunk. The second anterior region may be removably couplable to the first anterior region at a trunk attachment area to don the trunk garment about the trunk of the user. Further, the wraparound portion may define a mitt opening proximate the second anterior end region to receive a hand of the user to move the wraparound portion about the trunk of the user Still further, the trunk garment may further include, or comprise, a sacrificial attachment portion removably coupled to the first and second anterior regions. The removable coupling between the sacrificial attachment portion and the first anterior region may be stronger than the removable coupling between the sacrificial attachment portion and the second anterior region.

In one or more embodiments, the trunk garment may include, or comprise, a plurality of thigh strap portions for each of the user's legs that extend across an anterior side of the user's thighs and further may be removably couplable to a thigh attachment region of the trunk garment to don the trunk garment about the thighs of the user. Also, the plurality of thigh strap portions may define a gap between at least two thigh strap portions.

In one or more embodiments, the leg garment may extend from an upper end region to a lower end region. The upper end region may be located, or positioned, proximate at least a femoral region of the leg of the user when the leg garment is donned and the lower end region may be located, or positioned, proximate one or more of the crural region, tarsal region, the pedal region, and the digital/phalangeal region of the leg of the user when the leg garment is donned. Additionally, the system may further include, or comprise, tubing operably coupled to the one or more leg pressure applying regions to transmit fluid to the one or more leg pressure applying regions, and the tubing may be coupled to and extend from the leg garment between the upper end region and the lower end region.

Another exemplary compression garment system may include, or comprise, at least one leg garment and tubing. The leg garment may be donned about a right or left leg of the user to apply compression to the leg, and may include, or comprise, one or more leg pressure applying regions controllable to apply pressure to at least a portion of the leg. The leg garment may extend from an upper end region to a lower end region. The upper end region may be positioned, or located, proximate at least a femoral region of the leg of the user when the leg garment is donned and the lower end region may be positioned, or located, proximate one or more of the crural region, tarsal region, the pedal region, and the digital/phalangeal region of the leg of the user when the leg garment is donned. The tubing may be operably coupled to the one or more leg pressure applying regions to transmit fluid to the one or more leg pressure applying regions, and the tubing may be coupled to and may extend from the leg garment between the upper end region and the lower end region.

In one or more embodiments, the system may further include, or comprise, a strain relief portion removably coupled to the leg garment and removably coupled to the tubing to relieve strain from the operably coupling between the one or more leg pressure applying regions and the tubing. Further, one or more embodiments, the leg garment may include one or more loop portions proximate the upper end region of the leg garment to be grasped by a user when donning the leg garment to assist in donning the leg garment.

In one or more embodiments, the leg garment may include, or comprise, a plurality of leg strap portions that extend across at least a portion of the user's leg that are removably couplable to a leg attachment area of the leg garment to don the leg garment about the leg of the user and at least one loop portion coupled to at least one leg strap portions to be grasped by a user when donning the leg garment. Further, the at least one loop portion may include, or comprise, a plurality of loop portions, and each of the plurality of loops portions may include, or comprise, an identifier to distinguish each loop portion from each other.

In one or more embodiments, the leg garment may include, or comprise, a plurality of leg strap portions, and each of the plurality of leg strap portions may extend across at least a portion of the user's leg and may be removably couplable to a leg attachment area of the leg garment to don the leg garment about the leg of the user. Further, the leg garment may include, or comprise, a plurality of sacrificial attachment portions, and each of the plurality of sacrificial attachment portions may correspond to a different leg strap portion of the plurality of leg strap portions and may be removably coupled to the leg garment at the leg attachment area. Each of the plurality of leg strap portions may be removably couplable to the corresponding the sacrificial attachment portion. The removable coupling between the plurality of sacrificial attachment portions and the leg garment may be stronger than the removable coupling between the plurality of sacrificial attachment portions and the plurality of leg strap portions.

In one or more embodiments, the leg garment may further include, or comprise, a calf garment portion, a foot garment portion, and a heel element. The calf garment portion may be donned about a crural region of the leg of the user to apply compression to the crural region, and the leg pressure applying regions of the calf garment portion may be controllable to apply pressure to a portion of the crural region of the leg of the user. The foot garment portion may be donned about a pedal region of the leg of the user to apply compression to the pedal region, and the leg pressure applying regions of the foot garment portion may be controllable to apply pressure to a portion of the pedal region of the leg of the user. The heel element coupling the calf garment portion to the foot garment portion may be configured to receive the heel of the leg of the user. Further, in at least one embodiment, the heel element may define a curvature to follow the curvature of the tarsal region of the leg of the user to receive the heel of the leg of the user and to provide curvature of the leg garment from the crural region to the pedal region of the leg of the patient when the leg garment is donned.

In one or more embodiments, the leg garment may include, or comprise, a strap element to receive a portion of the foot of the other leg of the user to assist in removing the leg garment from the user's leg. The strap element may be positioned, or located, closer to the lower end region than the upper end region.

In one or more embodiments, the system may further include, or comprise, a controller to control pressure applied by at least one of the one or more trunk pressure applying regions and the one or more leg pressure applying regions to move lymph from at least one of the trunk and the leg.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
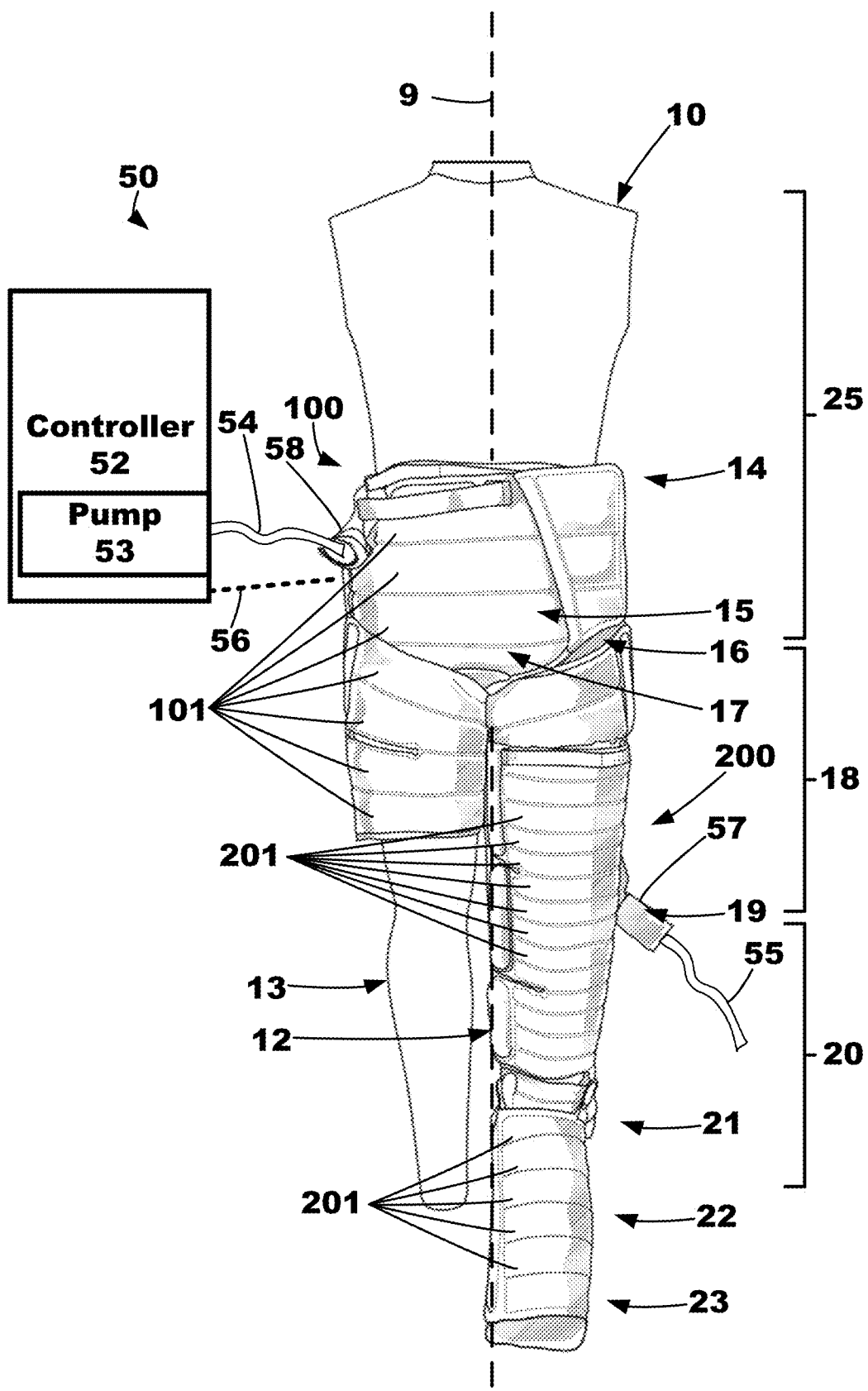
FIG. 1 is a front perspective of an exemplary compression system including a trunk garment and a leg garment located on a body.

In the following detailed description of illustrative embodiments, reference is made to the accompanying figures of the drawing, which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary apparatus, systems, structures, and methods shall be described with reference to FIGS. 1-18. It will be apparent to one skilled in the art that elements from one embodiment may be used in combination with elements of the other embodiments, and that the possible embodiments of such apparatus, systems, structures, and methods using combinations of features set forth herein is not limited to the specific embodiments shown in the Figures and/or described herein. Further, it will be recognized that the embodiments described herein may include many elements that are not necessarily shown to scale. Still further, it will be recognized that the size and shape of various elements herein may be modified but still fall within the scope of the present disclosure, although certain one or more shapes and/or sizes, or types of elements, may be advantageous over others.

The present disclosure relates generally to compression garments that include garment portions that are configured to be donned on at least a portion of a body (e.g., person, animal, etc.) and configured to apply pressure to that portion of the body, compression garment systems that include compression garments and apparatus for controlling pressure applied to at least a portion of a body, and methods using such compression garments and compression garment systems (e.g., methods of donning a garment, methods of controlling pressure applied to the body, etc.)

Compression garment systems (e.g., such as compression garments described in U.S. Pat. No. 6,179,796 entitled "Lymphedema treatment system," U.S. Pat. No. 6,645,165 entitled "Lymphedema treatment system," U.S. Pat. No. 6,860,862 entitled "Lymphedema Treatment System," and U.S. Pat. No. 6,966,884 entitled "Lymphedema Treatment System," which are herein incorporated by reference and which may modify and be modified with features described herein) may be used for various reasons including therapy for people with lymphedema, animals requiring therapy, wound therapy, etc. As used herein, the term body refers to not only humans but any other animal species that may benefit from the concepts and features described herein. These compression garments may be placed around at least a portion of an individual's body and used to apply pressure to the body at an affected extremity (e.g., leg, head, neck, arm, torso, a shoulder, etc.). Some embodiments described herein may include a compression system having a garment configured to be positioned on (e.g., wrapped around, placed adjacent, located in proximity to, etc.) at least a portion of a body (e.g., trunk, leg, foot, arm, torso, shoulder, head, neck, etc.). The compression garments may be donned (e.g., put on) and doffed (e.g., taken off) by individuals themselves or with help from others. The garment may also include one or more chambers (e.g., cells, compartments, sealed volumes, bladders etc.) distributed (e.g., distributed throughout, distributed in concentric patterns "radiating" away from a central point or axis, along a length, etc.) of the garment configured to receive a fluid (e.g., air) to perform compression therapy.

The compression therapy provided by the compression garment systems may help to treat lymphedema. Lymphedema is a condition of localized fluid retention and tissue swelling that may be inherited, caused by cancer treatments, caused by parasitic infections, injury, etc. For example, lymphedema of the legs may cause swelling around the feet, ankles, calves, knees, thighs, etc. Compression garments described herein covering the leg and trunk may be used by an affected individual to provide a therapeutic benefit. Specifically, the compression garments may be configured to manipulate lymph nodes or vessels by applying pressure to move lymph toward more beneficial locations (e.g., toward drainage areas, away from affected regions, etc.). For example, compression therapy using the systems described herein may be performed around the leg and trunk regions to help treat lymphedema in the leg and trunk regions by, e.g., moving lymph upward towards the upper torso, moving lymph downward away from the upper torso, etc.

The compression garments described herein may be configured to apply pressure to the affected regions of the body to apply compression therapy. The compression garments may include various portions that each includes controllable pressure applying regions. Each controllable pressure applying region may be configured to apply pressure to a specific portion of the body (e.g., at a specific time during therapy). The controllable pressure applying regions may work in combination with one another to help provide therapy by applying a sequence of pressures on the body that moves lymph in a desired direction (e.g., from the feet towards the trunk, from the trunk towards the feet, from the feet towards the calf, from the ankle towards the thigh, etc.). Such application of a sequence of pressures on the body that moves lymph (e.g., pressure being applied to one or more portions of the legs, feet, and trunk, at different times during a compression therapy period) may be referred to as applying dynamic pressure to the body. The sequence of pressures may be referred to as pressure gradients, e.g., from a distal region (e.g., feet, toes, ankle, etc.) to a proximal region (e.g., trunk, torso, etc.). Additionally, in some embodiments, dynamic pressure may not be applied sequentially, and instead, be applied non-sequentially as will be further described herein.

The controllable pressure applying regions of the compression garments may also apply static pressure to the body. For example, the compression garments may apply a constant pressure when a portion of the garment is positioned on the body over a therapy time period (e.g., static pressure over the therapy time period) or may apply a pressure that may be controlled to change over time during the therapy time period (e.g., dynamic pressure). In one or more embodiments, the dynamic pressure may be applied to the portion of the body through one or more chambers in the compression garment. The one or more chambers may be configured to receive fluid. Alternately, or in combination with one or more fluid receiving chambers, such pressures may be applied using one or more actuatable elements in the compression garment configured to apply pressure to the body (e.g., electrically controlled materials suitable to provide compression).

An exemplary compression garment system 50 including a trunk compression garment 100 configured to be positioned around at least a portion of a trunk 25 and legs 12, 13 of a human body 10 and a leg compression garment 200 configured to be positioned around at least a portion of the left leg 12 of the human body 10 is shown in FIGS. 1-5. The trunk garment 100 and the leg garment 200 may be used in conjunction or apart from each other to provide compression therapy to the body 10. Although, in the embodiment depicted, the trunk garment 100 and one leg garment 200 are donned on the body 10, it is to be understood that what is depicted in FIGS. 1-5 is only one configuration and the trunk and leg garments 100, 200 may be used in many other configurations. For example, two leg garments 200 may be used at the same time with or without the trunk garment 100. Further, for example, the trunk garment 100 may be used by itself. Still further, for example, one leg garment 200 may be used about the right leg 12 with or without the trunk garment 100.

The trunk garment 100 and the leg garment 200 may each define, or include, a plurality of pressure applying regions that are controllable or configurable to apply pressure to portions of the body 10. For example, the trunk garment 100 may include trunk pressure applying regions 101 that are controllable or configurable to apply pressure to one or more portions or regions of the torso, or trunk, 25 such as, e.g., to the abdominal region 14, the pelvic region 15, the coxal region 16, the groin region 17, and the femoral region 18. For example, the leg garment 200 may include leg pressure applying regions 201 that are controllable or configurable to apply pressure to one or more portions or regions of the legs 12, 13 such as, e.g., to the femoral region 18, the patellar region 19, the crural region 20, the tarsal region 21, the pedal, or foot, region 22, and the digital/phalangeal region 23. In one or more embodiments, the trunk and leg garments 100, 200 may include an exterior material covering the pressure applying regions.

The one or more pressure applying regions 101, 201 may include fluid chambers or cells, pneumatic pressure applying regions, actuatable elements, hydraulic pressure applying regions, etc. In one or more embodiments, the one or more pressure applying regions 101, 201 may include one or more chambers configured to receive fluid, and the system 50 may further include a controller 52 configured to apply pressure to one or more portions or regions of the body 10 using the one or more chambers through the control of fluid provided thereto, e.g., fluid flow, air flow, etc. For example, the trunk garment 100 may include one or more trunk garment ports through which fluid may be provided to the one or more chambers via tubing 54, and the leg garment portion 200 may include one or more leg garment ports through which fluid may be provided to the one or more chambers via tubing 55.

Figure 2:
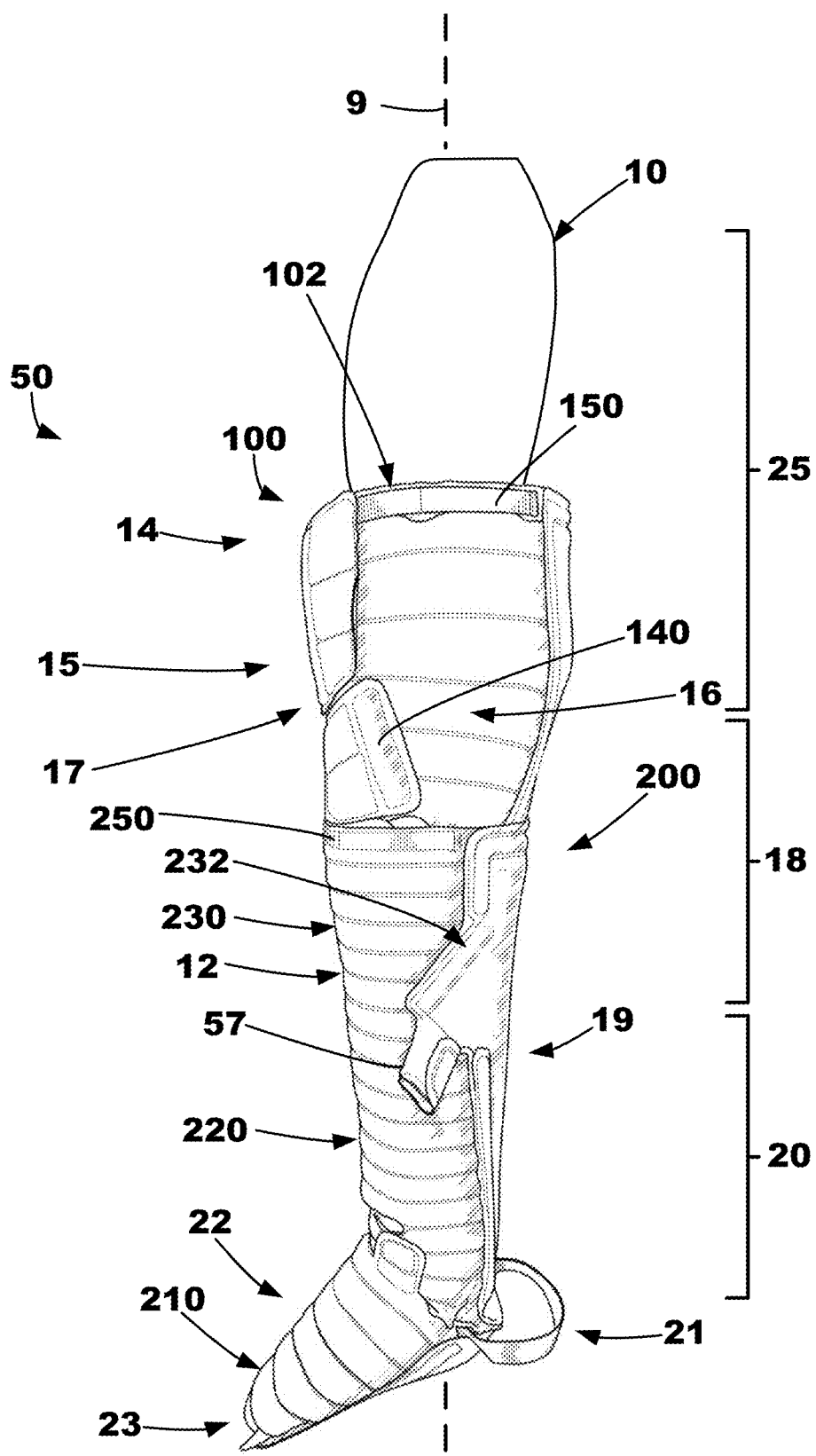
FIG. 2 is right perspective view of the system of FIG. 1.
Figure 3:
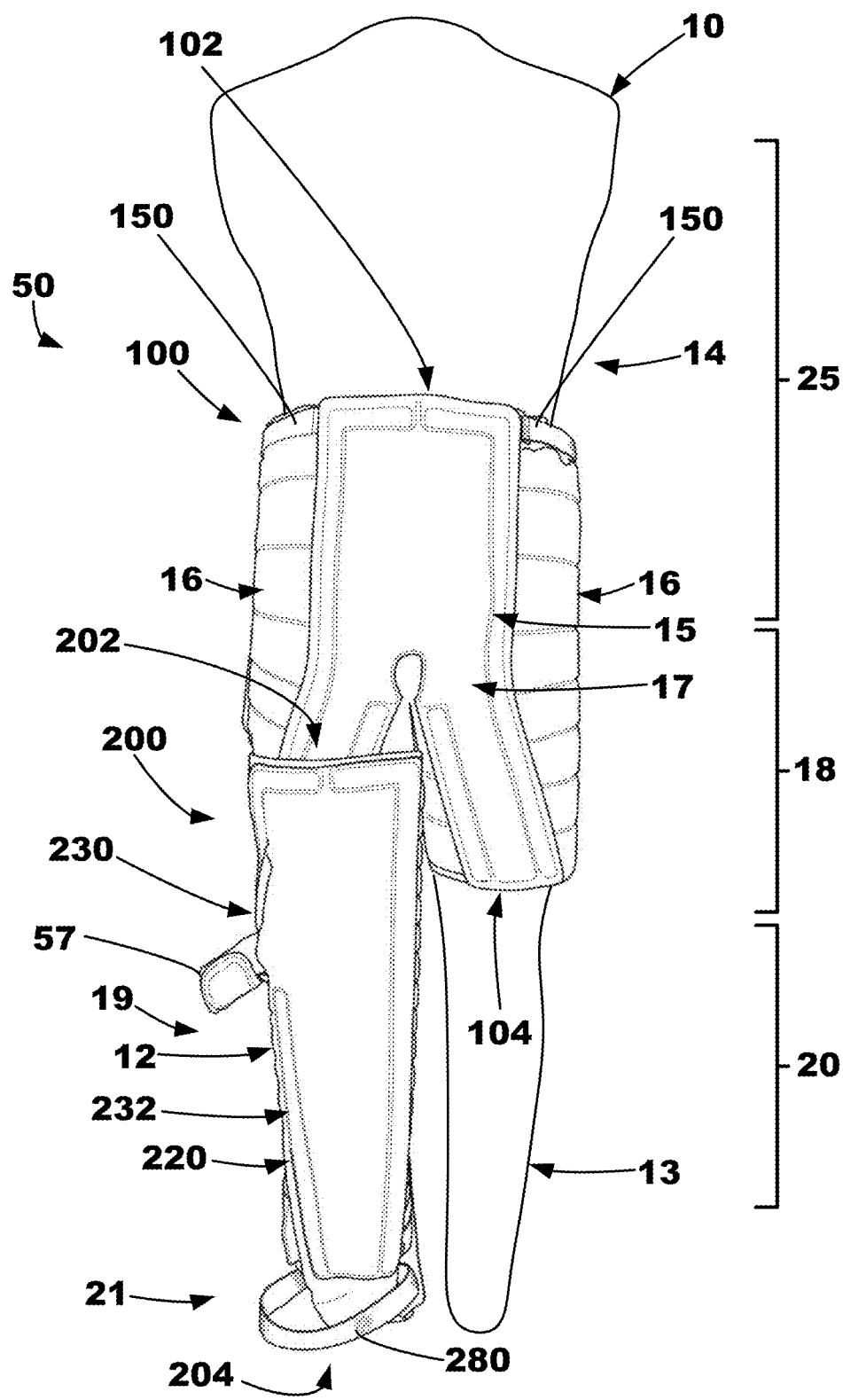
FIG. 3 is rear perspective view of the system of FIG. 1.
Figure 4:
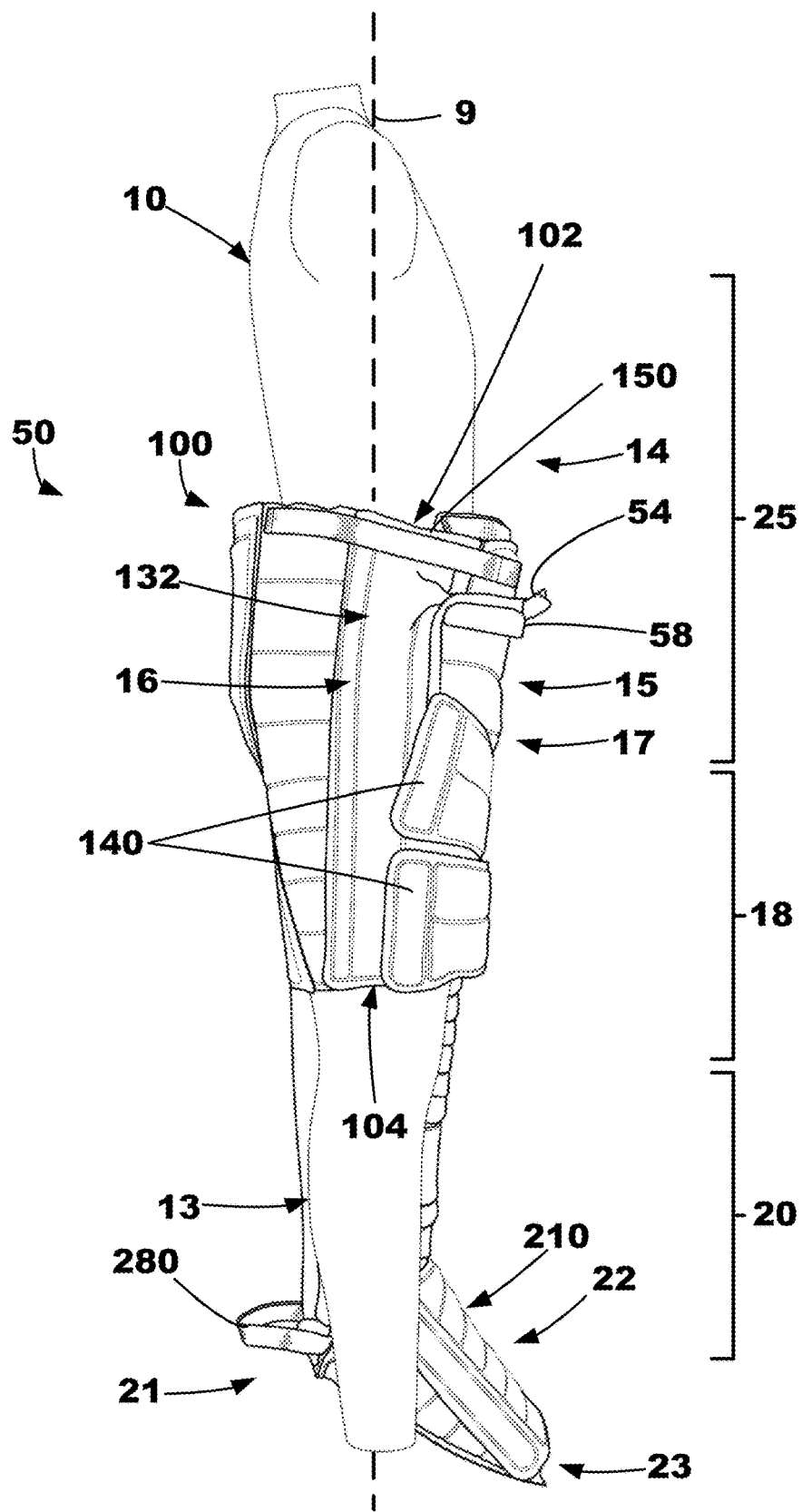
FIG. 4 is left perspective view of the system of FIG. 1.
Figure 5:
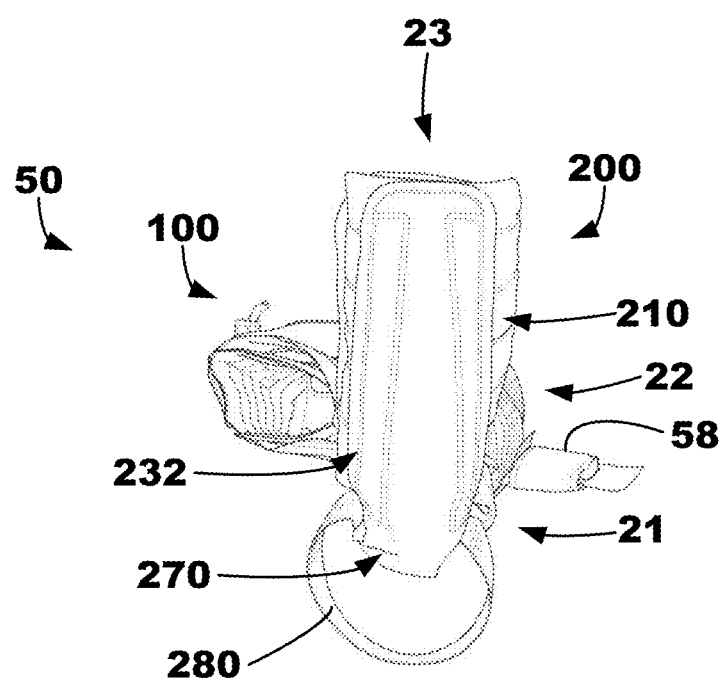
FIG. 5 is bottom perspective view of the system of FIG. 1.
Figure 6:
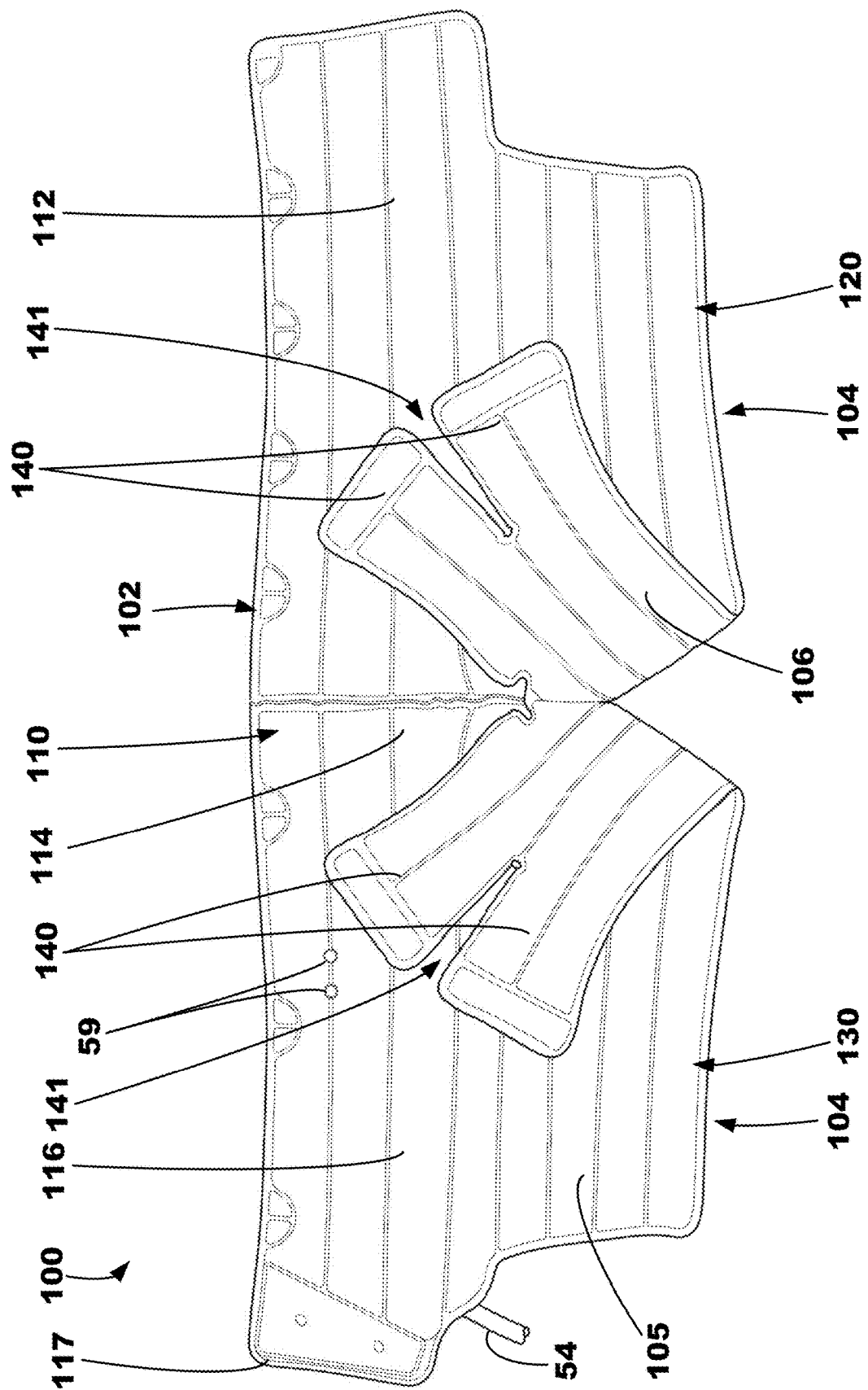
FIG. 6 is a perspective view of the trunk garment of the system of FIG. 1 in an open configuration prior to donning.
Figure 17:
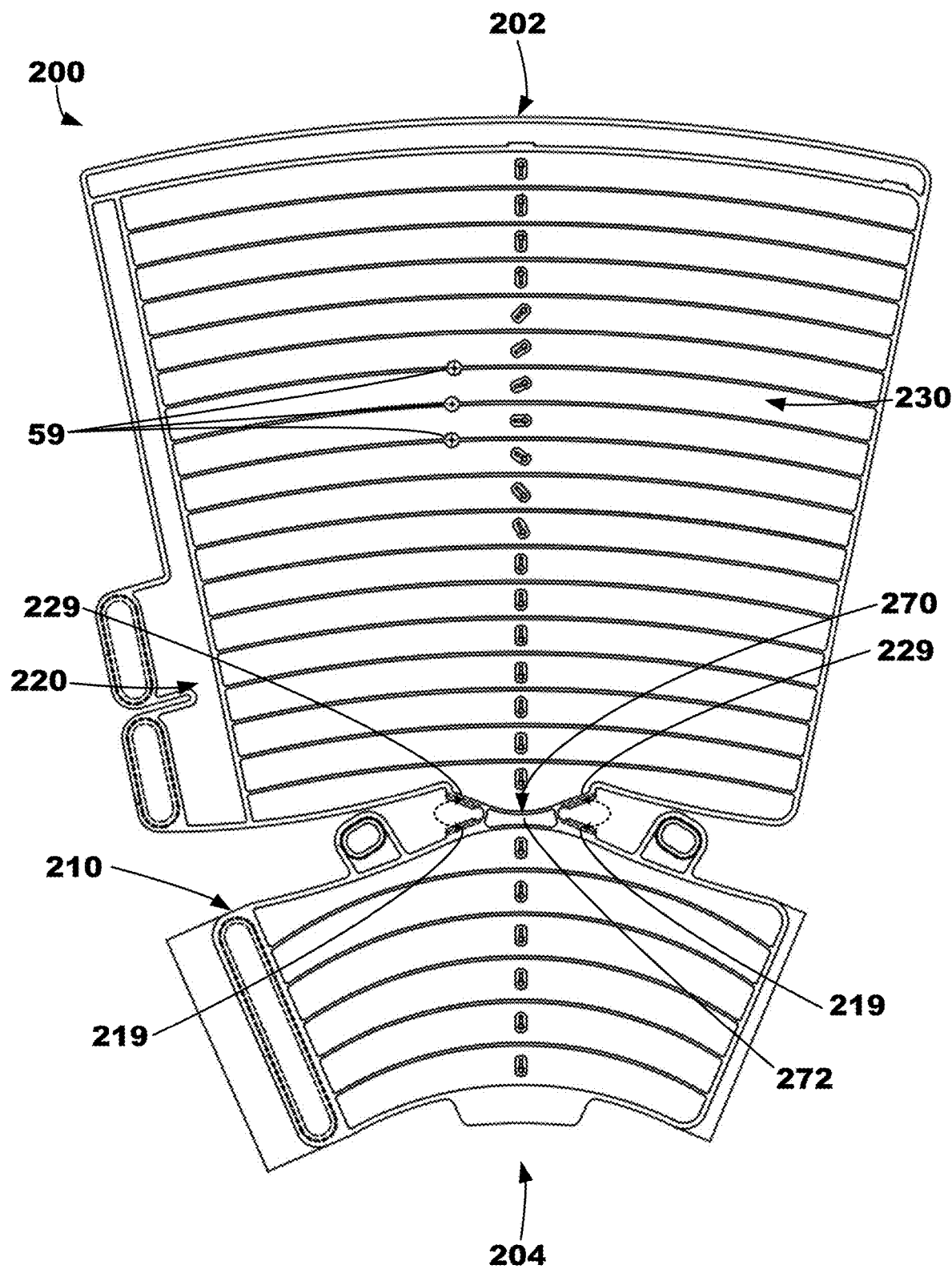
FIG. 17 is a plan view of another exemplary leg garment.

The system 50 may further include strain relief portions 57, 58 configured to relieve any strain applied to the tubing 55, 54, respectively. For example, the tubing 54, 55 may extend from a proximal end that is attached or coupled to the trunk garment 100 and leg garment 200, respectively, such that the tubing 54, 55, may be operably coupled to the pressure applying regions 101, 201, respectively, to a distal end that is coupled to a controller 52 for delivering fluid into the tubing 54, 55, and in turn, the pressure applying regions 101, 201. A user may pull on the distal end of the tubing 54, 55, which may apply unnecessary stress on the operably coupling of the tubing 54, 55 to the pressure applying regions 101, 201, and such unnecessary stress may loosen or break the operable couplings, which may lead to leaks, damage, etc. The strain relief portions 57, 58 may alleviate this issue by providing an alternative path for the stress applied to the tubing 55, 54. Specifically, the strain relief portions 57, 58 may be coupled (e.g., removably, fixedly coupled) to the garments 200, 100, and also coupled (e.g., removably, fixedly coupled) to each of the tubing 55, 54 proximate the leg garment 200 and the trunk garment 100. In this way, if the distal end of the tubing 54, 55 is pulled thereby applying strain to the tubing 54, 55, such strain will be transmitted, or transferred, to the trunk and leg garments 100, 200 via the strain relief portions 58, 57 such that the strain is reduced, or not transmitted, to the proximal end of the tubing 54, 55 and/or the operable coupling of the tubing 54, 55 to the pressure applying regions 101, 201. Further, in at least the embodiment depicted, the strain relief portions 57, 58 may be riveted to the leg and trunk garment 200, 100 using, e.g., polymer rivets 59 as shown in FIG. 6 on the trunk garment 100 and as shown in FIG. 17 on the leg garment 200. Such rivets 59 may extend through the garments 100, 200 and the strain relief portions 58, 57 to fixedly couple the garments 100, 200 to the strain relief portions 58, 57. Additionally, the strain relief portions 57, 58 may also be part of (e.g., continuously part of, a removably couplable portion of, etc.) a tubing cover 232, 132 (e.g., as shown in FIGS. 2-4) that may be removably coupled to the garments 200, 100 to, e.g., cover up tubing that runs, or extends, about the garments 200, 100 to each of the pressure applying regions 101, 201.

In at least one embodiment, the strain relief portions 57, 58 may be described as including, or comprising, two portions: a tongue element and a wraparound element. The tongue element may extend from a first end that is fixedly attached to the garment to a second end that is removably couplable to the wraparound element. The wraparound element may be configured to be wrapped around the tubing to secure itself to the tubing such that, e.g., movement of the tubing will also move the wrapround element. As the second end of the tongue element is couplable to the wraparound element, movement of the tubing will also move the tongue element. Since the first end of the tongue element is fixedly coupled, or secured, to the garment, movement of the tubing may be restricted by the strain relief portion, and thus, unnecessary movement or strain on the tubing may be directed to the garment itself through the strain relief portion without impacting the coupling of the tubing to the pressure applying regions.

Further, in one or more embodiments, the pressure applying regions 101, 201 may include one or more actuatable elements (e.g., non-fluid receiving regions) configured to apply pressure to the one or more body portions or regions (e.g., an electrical signal may be used to actuate an element within the garment, such as electrically actuatable fibers in the garment, such that the compartment including such fibers applies a pressure to a portion or region of the body). In one or more embodiments, the one or more pressure applying regions 101, 201 may include both one or more chambers configured to receive fluid and one or more actuatable elements.

Any number of pressure applying regions 101, 201, some of which are labeled in FIG. 1, may be configured in the trunk and leg garment 100, 200, respectively, such that the pressure applying regions 101, 201 may be controlled to move lymph as described herein. For example, as shown in FIGS. 1-15, the trunk garment 100 includes eight pressure applying regions 101 and the leg garment 200 includes twenty-two pressure applying regions 201. However, such pressure applying regions 101, 201 may include any number of different and separate chambers along the wrappable length of the garments 100, 200 and controllable to produce desired lymph movement (e.g., multiple chambers along the length of the trunk and leg garments 100, 200 to move lymph generally vertically in a downward or upward direction, etc.).

The controller, or control apparatus, 52 may be configured to control the pressure applied to one or more portions or regions of the body 10 using each of the pressure applying regions 101, 201 of the garments 100, 200. For example, the controller 52 may control the pressure applied to the one or more portions or regions of the body 10 by using each of the pressure applying regions 101, 201 independent from one another or at the same time. Further, for example, the pressure applying regions 101, 201 may be controlled in groups or combinations. In one or more embodiments, the controller 52 may be configured to control the pressure applying regions 101, 201 in a variety of different sequences (e.g., applying pressure in a predetermined manner) that may be, e.g., suitable for carrying out, or performing, lymphedema therapy.

Further, the controller 52 may control the pressure based on one or more pressures measured by one or more pressure sensors associated with, or part of, the controller 52 and the garments 100, 200 (e.g., sensors provided in the garment 100, 200 proximate the pressure applying regions 101, 201). One or more compression garments that may be modified with features (e.g., sensors) described herein may be similar to and include one or more features found in U.S. Pat. No. 6,860,862 entitled "Lymphedema Treatment System," U.S. Pat. No. 6,966,884 entitled "Lymphedema Treatment System," U.S. Pat. No. 6,179,796 entitled "Lymphedema treatment system," and U.S. Pat. No. 6,645,165 entitled "Lymphedema treatment system," which are herein incorporated by reference.

In one or more embodiments, the controller 52, which may include one or more processors employing one or more programs or routines carrying out one or more methods or processes and implemented with one or more types of memory, may be described as being configured to control the system and/or one or more elements thereof (e.g., providing compression therapy by the one or more pressure applying regions, etc.). In one or more embodiments, the controller 52 may be configured to control the compression system using wired and/or wireless technology.

The methods and/or logic and/or configurations described in this disclosure, including those attributed to the systems, or various constituent components, may be implemented, at least in part, in hardware, software, firmware, or any combination thereof. For example, various aspects of the techniques may be implemented within one or more processors, including one or more microprocessors, microcontrollers, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices (e.g., within the system, outside of the system, or a combination of both) to support the various operations and functions described in this disclosure. In addition, any of the described components may be implemented together or separately as discrete but interoperable logic devices. Description of different features is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

Further, the compression garment system 50 may include a pump 53 that may be controlled by the controller 52 to provide a fluid to/from the plurality of pressure applying regions 101, 201, which may be a plurality of chambers. For example, the pump 53 may be connected to the plurality of chambers corresponding to the plurality of pressure applying regions 101, 201 by tubing 54, 55 so as to provide flow of fluid thereto or removal of fluid therefrom.

Further, in one or more embodiments, the controller 52 may be connected to one or more components of the compression garment system 50 via one or more electrical lines and/or wirelessly, as represented generally by dashed line 56 in FIG. 1. For example, the controller 52 may be connected to communicate and control the pressure applying regions (e.g., such as electrically actuatable pressure applying regions of the garment configured to apply pressure to the body) either with use of physical electrical connections and/or wirelessly.

The pressure applying regions 101, 201 of the garments 100, 200 may be described as being controllable since the pressure applying regions 101, 201 are under control of controller 52. Thus, the system 50, using the controller 52, may be configured to provide compression therapy to an individual (e.g., a patient) wearing the garments 100, 200 such that lymph flows throughout the body 10 in desired directions, e.g., such as from the leg or legs 12, 13 to the trunk, or torso, 25 of the body 10, from the trunk, or torso, 25 to the leg or legs 12, 13 of the body 10, etc. In other words, by controlling the pressure applying regions 101, 201 in a variety of different sequences (e.g., applying pressure in a predetermined manner), for example, lymph may flow generally from the legs 12, 13 and lower trunk of the body 10 towards the upper trunk of the body 10. The direction of lymph flow from the legs 12, 13 to the trunk 25 of the body 10 may provide relief to an individual by moving excess lymph from the legs 12, 13, and ultimately, moving such lymph towards and into one or more regions of the trunk 25 such as, e.g., the right axillary nodes located proximate a right under arm region and the left axillary nodes located proximate a left under arm region.

The pressure applying regions 101, 201 of the trunk and leg garments 100, 200 can be described as either providing a normal, or first, pressure value or providing an increased, or second, pressure value (e.g., the increased, or second, pressure value being greater than the normal, or first, pressure value). In at least one embodiment, the first, or normal, pressure value for the pressure applying regions 101, 201 of the trunk and leg garments 100, 200 is about 0 mmHG, about 10 mmHG, about 20 mmHG, about 30 mmHG, about 50 mmHg, about 60 mmHG, etc. (over atmospheric pressure) and the second, or increased, pressure value for the pressure applying regions 101, 201 of the trunk and leg garments 100, 200 is about 30 mmHG, about 40 mmHG, about 45 mmHG, about 50 mmHG, about 70 mmHg, about 100 mmHG, etc. (over atmospheric pressure). For example, the first, or normal, pressure value for the pressure applying regions 101, 201 of the trunk and leg garments 100, 200 may be greater than or equal to about 0 mmHg, greater than or equal to about 5 mmHg, about 10 mmHg, greater than or equal to about 20 mmHg, greater than or equal to about 30 mmHg, greater than or equal to about 40 mmHg, greater than or equal to about 50 mmHg, greater than or equal to about 60 mmHg, etc. Further, for example, the first, or normal, pressure value for the pressure applying regions 101, 201 of the trunk and leg garments 100, 200 may be less than or equal to about 80 mmHg, less than or equal to about 70 mmHg, less than or equal to about 55 mmHg, less than or equal to about 45 mmHg, less than or equal to about 35 mmHg, etc. For example, the second, or increased, pressure value for the pressure applying regions 101, 201 of the trunk and leg garments 100, 200 may be greater than or equal to about 20 mmHg, greater than or equal to about 40 mmHg, greater than or equal to about 50 mmHg, greater than or equal to about 60 mmHg, greater than or equal to about 70 mmHg, greater than or equal to about 80 mmHg, greater than or equal to about 90 mmHg, greater than or equal to about 105 mmHg, greater than or equal to about 120 mmHg, greater than or equal to about 140 mmHg, greater than or equal to about 160 mmHg, greater than or equal to about 190 mmHg, etc. For example, the second, or increased, pressure value for the pressure applying regions 101, 201 of the trunk and leg garments 100, 200 may be less than or equal to about 300 mmHg, less than or equal to about 250 mmHg, less than or equal to about 200 mmHg, less than or equal to about 175 mmHg, less than or equal to about 150 mmHg, less than or equal to about 130 mmHg, less than or equal to about 110 mmHg, less than or equal to about 100 mmHg, less than or equal to about 95 mmHg, less than or equal to about 85 mmHg, less than or equal to about 75 mmHg, less than or equal to about 65 mmHg, less than or equal to about 45 mmHg, less than or equal to about 30 mmHg, etc.

The trunk garment 100, which is depicted by itself in FIGS. 6-9, may be generally described as being positionable relative to the body 10 to provide compression therapy to one or more of the mid and lower regions of the trunk, or torso, 25, and the upper regions of the legs 12, 13 of the body 10. More specifically, the trunk garment 100 may be described as extending from an upper end region 102 to a lower end region 104 generally along an axis 9 that extends along the body 10 when the trunk garment 100 is donned.

When the trunk garment 100 is donned about the body 10, the upper end region 102 may be positioned, or located, in an area proximate the abdominal region 14 (e.g., including the stomach area), the pelvic region 15, and/or the coxal region 16 depending on the size of the trunk garment 100 relative the size of the body 10. In one or more embodiments, the trunk garment 100 may be configured such that the upper end region 102 is positioned, or located, proximate at least the pelvic region 15 of the body 10. In one or more embodiments, the trunk garment 100 may be configured such that the upper end region 102 is positioned, or located, proximate at least the umbilicus, or naval, of the body 10. In other words, the trunk garment 100 may extend in an upward direction along the axis 9 to at least the pelvic region 15 of the body 10 or at least the umbilicus, or naval, of the body 10.

When the trunk garment 100 is donned about the body 10, the lower end region 104 may be positioned, or located, in an area proximate an upper area of the femoral region 18 (e.g., thigh) of each of the legs 12, 13. The lower end region 104 may be positioned more proximal (e.g., higher) or more distal (e.g., lower) on the body's legs 12, 13 depending on the size of the trunk garment 100 relative the size of the body 10. In one or more embodiments, the trunk garment 100 may be configured such that the lower end region 104 is positioned, or located, proximate the patellar region, or knee, 19 of the body 10. In one or more embodiments, the trunk garment 100 may be configured such that the lower end region 104 is positioned, or located, proximate at least an area positioned about halfway between the pelvic region 15 and the patellar region 19 of the body 10. In one or more embodiments, the trunk garment 100 may be configured such that the lower end region 104 is positioned, or located, at least beyond the coxal region 16 of the body 10.

In other words, the lower end region 104 of the trunk garment 100 may extend along a least a portion of the upper area of the femoral region 18 of the legs 12, 13 such as, e.g., the coxal region 16, and in some embodiments, may distally extend further along the legs 12, 13, to an area about halfway between the pelvic region 15 and the patellar region 19 of the body 10 or all the way to the patellar region 19 of the body 10.

In one or more embodiments, the trunk garment 100 may be configured such that the tubing 54 is coupled to and extends from the trunk garment 100 between the upper end region 102 and the lower end region 104 as opposed to, e.g., extending from the upper or lower end regions 102, 104, which may be cumbersome. In other words, the tubing 54 may be coupled to and extend from the trunk garment 100 in a middle region that is between the lower end region 104 and the upper end region 102.

The trunk garment 100 may further include one or more or a plurality of loop portions 150 coupled to and extending from the upper end region 102. The loop portions, or webbing, 150 may be configured to be grasped by a user when donning or removing the trunk garment 100. In one or more embodiments, the loop portions 150 may be located substantially all the way around the trunk garment 100. In one or more embodiments, the loop portions 150 may only be located in one or more selected areas about the trunk garment 100 such as one or more of the left anterior side, the right anterior side, the left side, and the right side. In at least one embodiment, the loop portions 150 may be woven nylon strapping that is stitched to the upper end region 102 of the trunk garment 100.

The trunk garment 100 is depicted in an unwrapped configuration in FIG. 6 exposing an inside surface 105 of the trunk garment 100. The inside surface 105 is the surface that is substantially in contact with the body 10 of the user when the trunk garment 100 is donned. The outside surface 106, which is opposite the inside surface 105 (e.g., substantially faces the opposite direction than the inside surface 105), is configured to face outwardly away from the body 10 of the user when the trunk garment 100 is donned.

In the embodiment described herein, the trunk garment 100 may be described as including a wraparound portion 110, a left upper leg portion 120, and a right upper leg portion 130 as shown in FIG. 6. The wraparound portion 110 may define the upper end region 102, and the left and right upper leg portions 120, 130 may define the lower end region 104. The wraparound portion 110 may be configured to be wrapped about at least a portion of the trunk 25 of the body 10, the left upper leg portion 120 may be configured to be wrapped about at least a portion of the left leg 12 of the body 10, and the right upper leg portion 130 may be configured to be wrapped about at least a portion of the right leg 13 of the body 10.

Each of the wraparound portion 110, left upper leg portion 120, and right upper leg portion 130 may be configured to be at least partially wrapped about a portion of the body 10, and may include a plurality of pressure applying regions 101 concentrically positioned about the body portions of the user when the trunk garment 100 is donned. More specifically, each of the trunk pressure applying regions 101 may be generally described as lying substantially in a plane that is substantially perpendicular to the axis 9 around the trunk 25 and upper portion of the legs 12, 13 when the trunk garment 100 is donned by a user. The pressure applying regions 101 of the trunk garment 100 may be described as being concentric and parallel such that the pressure applying regions 101 direct fluid unidirectionally vertically either up across the umbilical watershed for lower extremity therapy or down towards the inguinal watershed for upper extremity therapy as opposed to designs that directs flow vertically and laterally (e.g., designs that have curved chambers that do not lie in a plane a plane that is substantially perpendicular to the axis 9). In other words, the concentric, parallel pressure applying regions 101 may not be configured to direct fluid (e.g., lymph) substantially sideways or substantially perpendicularly to the axis 9, and instead, may be configured to direct fluid (e.g., lymph) substantially vertically or substantially parallel to the axis 9.

The trunk garment 100 may further include a plurality of thigh straps 140 extending from and coupled to the left and right upper leg portions 120, 130. Each of the thigh straps 140 may be grasped, moved, and removably coupled to a region of the left and right upper leg portions 120, 130 to define the left and right upper leg openings 121, 131, respectively, for receiving the femoral region 18 (e.g., thigh) of the legs 12, 13, respectively. When the trunk garment 100 is donned about the body 10, the thigh straps 140 may extend across at least an anterior side of the femoral regions 18 of the legs 12, 13 of the body 10. More specifically and as shown in this embodiment, two thigh straps 140 are coupled to and extend from each of the left and right upper leg portions 120, 130, and are configured to be removably coupled to thigh attachment regions of the left and right upper leg portions 120, 130, respectively. The removable coupling between the thigh straps 140 and the thigh attachment regions may be facilitated using any suitable removable connection apparatus such as, e.g., hook-and-loop fasteners. For example, the thigh strap 140 may include the "hook" portion of a hook-and-loop fastener while the thigh attachment regions may include the "loop" portion of a hook-and-loop fastener. More specifically, the outer surface 106 of the trunk garment 100 may be material that may be or may act as the "loop" portion of a hook-and-loop fastener.

The thigh straps 140 may be used to adjust the size of the left and right upper leg openings 121, 131 of the left and right upper leg portions 120, 130, respectively, to fit about the left and right legs 12, 13 of the user, e.g., at the desired level of fitment, tightness, snugness, etc. The thigh straps 140 may be used to adjust the size of the left and right upper leg openings 121, 131 of the left and right upper leg portions 120, 130 during the first, or initial, instance a user uses the trunk garment 100, and thereafter, a user may not adjust the thigh straps 140 when donning the trunk garment 100. Instead, the user may locate, or slip, each of the user's legs 12, 13 into the left and right upper leg openings 121, 131 of the left and right upper leg portions 120, 130 and then pull the trunk garment 100 upward (e.g., using the loop portions 150) towards the user's trunk 25 similar to donning a pair of shorts or pants. In this way, the left and right upper leg portions 120, 130 may remain adjusted to the particular sizing that the user desires. Nonetheless, if a user desires to change the fitment, or size, of the left and right upper leg openings 121, 131 of the left and right upper leg portions 120, 130, a user may remove the thigh straps 140 from being removably coupled to the thigh attachment regions of the left and right upper leg portions 120, 130, move the thigh straps 140 relative to the left and right upper leg portions 120, 130 to achieve the desired level of fitment, and then re-couple the thigh straps 140 to the thigh attachment regions. Further, each of the thigh straps 140 may be adjusted one-at-time or simultaneously.

Although two thigh straps 140 are coupled to and extend from each of the left and right upper leg portions 120, 130 as shown, it is to be understood than the exemplary trunk garment 100 described herein may include any number of thigh straps 140 coupled to and extending from each of the left and right upper leg portions 120, 130. In one or more embodiments, the trunk garment 100 may include one thigh strap 140 coupled to and extending from each of the left and right upper leg portions 120, 130. In one or more embodiments, the trunk garment 100 may include a plurality of thigh straps 140 coupled to and extending from each of the left and right upper leg portions 120, 130 such as, e.g., two or more thigh straps, three or more thigh straps, five or more thigh straps, etc.

A gap, or a space, 141 may be defined between the thigh straps 140 such that, e.g., each of the thigh straps 140 may operate somewhat independently from each other when being used to adjust the size of the left and right upper leg openings 121, 131 of the left and right upper leg portions 120, 130, respectively. In other words, the trunk garment 100 may be described as providing notched thigh straps 140 or slits 141 in such thigh flaps 140 that allow for improved coverage and compression in the groin region 17.

The wraparound portion 110 of the trunk garment 100 may be configured to be at least partially wrapped about one or more of the abdominal region 14, the pelvic region 15, the coxal region 16, the groin region 17, and an upper part of the femoral region 18 of the body 10. The wraparound portion 110 may be described as extending from a first anterior region 112 to a posterior region 114 to a second anterior region 116 as shown in FIG. 6. The first anterior region 112 may be configured to be located proximate the anterior of the body 10 of the user in substantially direct contact with the body 10. Substantial direct contact may be described as being in "contact" with the body 10 such that no other portion or region of the trunk garment 100 is located between the portion and the body 10 of the user. The posterior region 114 may be configured to be located proximate the posterior of the body 10 of the user in substantially direct contact with the body 10. And, the second anterior region 116 may be configured to be located proximate the anterior of the body 10 of the user over the first anterior region 112 when the trunk garment 100 is donned by the user. Thus, while the first anterior region 112 of the wraparound portion 110 may be described as being adjacent, or in substantially direct contact, with the anterior of the body 10 of the user, the second anterior region 114 of the wraparound portion 110 may not be described as being adjacent, or in substantially direct contact, with the anterior of the body 10 of the user because the first anterior region 112 is located between the second anterior region 116 and the body 10 of the user.

Figure 7A:
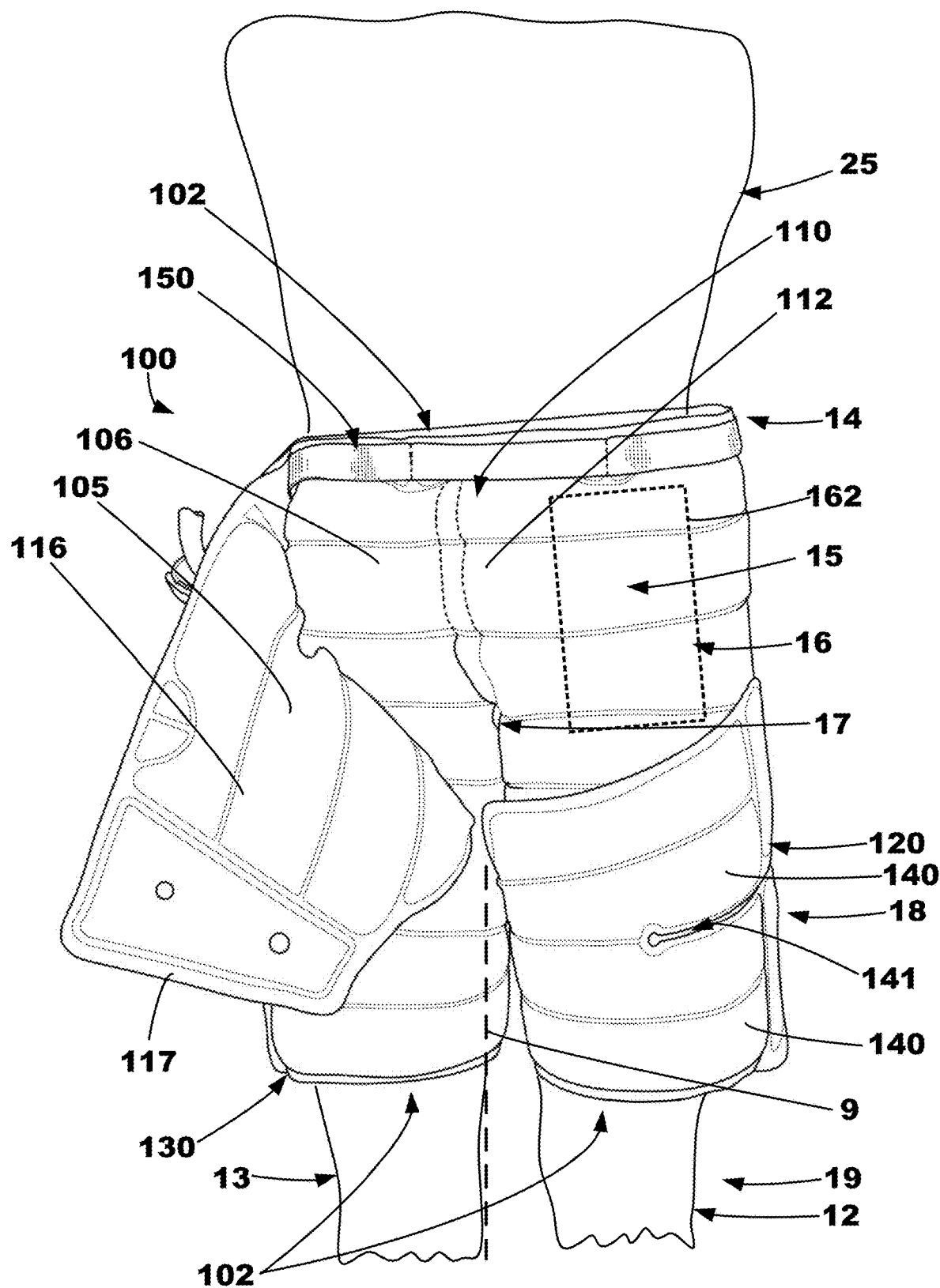
FIG. 7A is a front perspective view of the trunk garment of FIG. 6 partially donned on a body and including a sacrificial attachment portion attached to an attachment region.

For example, the trunk 100 garment is partially donned about the user in FIG. 7, and the first anterior region 112 is located proximate the anterior of the body 10 of the user and in substantially direct contact with the body 10 as shown and the posterior region 114 is located proximate the posterior of the body 10 of the user and in substantially direct contact with the body 10, which is not shown in this view. Since the trunk garment is only partially-donned, the second anterior region 116, however, is hanging from the remainder of the trunk garment 100.

To completely don the trunk garment 100, the second anterior region 116 may be extended across the anterior side of the user's body 10 over the first anterior region 112 and removably coupled to the first anterior region 112 at a trunk attachment area 162. The removable coupling between the first anterior portion 112 and the second anterior portion 116 may be facilitated using any suitable removable connection apparatus such as, e.g., hook-and-loop fasteners. For example, the second anterior region 116 may include the "hook" portion of a hook-and-loop fastener while the first anterior region 112 may include the "loop" portion of a hook-and-loop fastener. More specifically, the outer surface 106 of the trunk garment 100 may be material that may be or may act as the "loop" portion of a hook-and-loop fastener of the trunk attachment area 162.

Figure 7B:
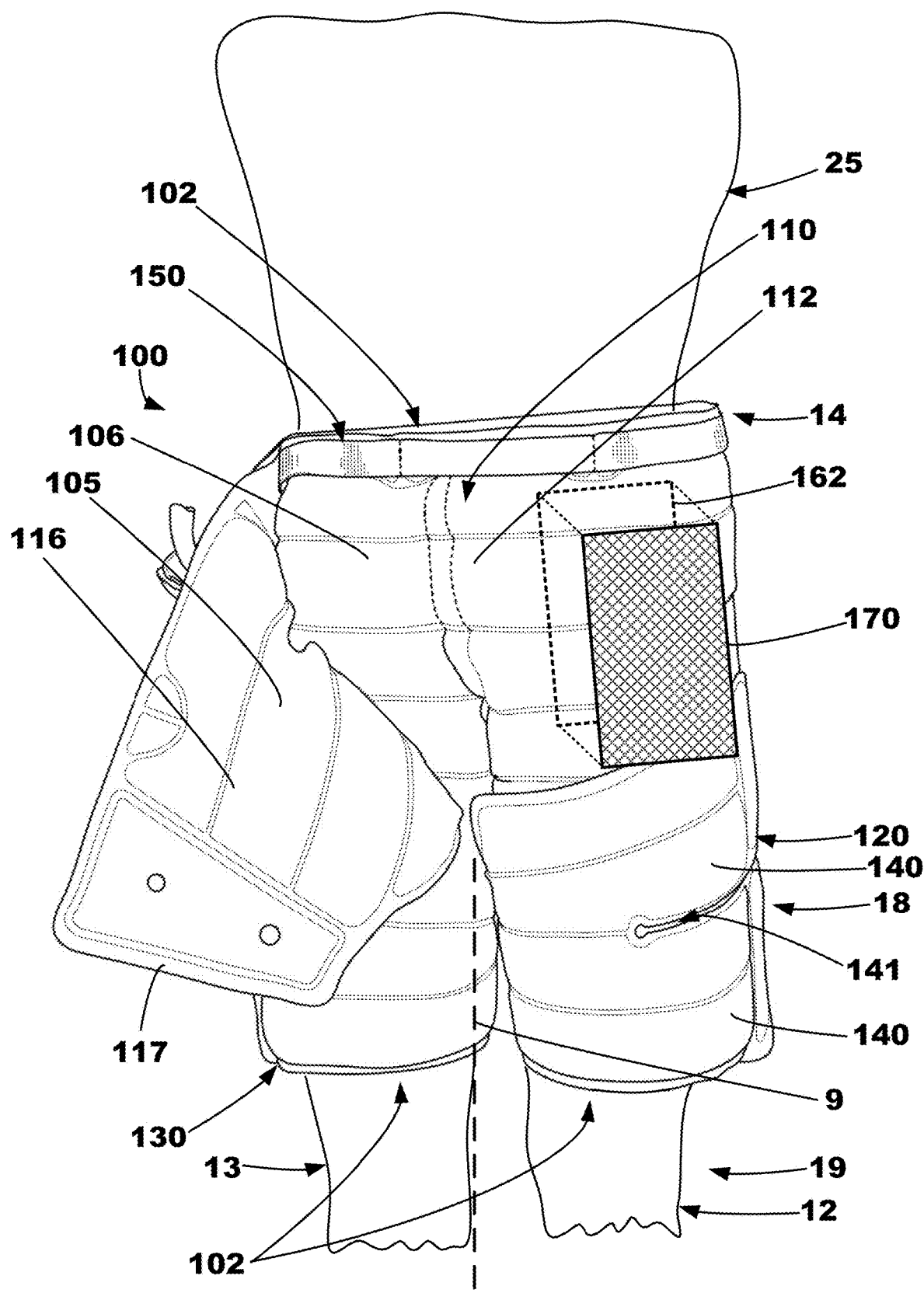
FIG. 7B is a front perspective view of the trunk garment of FIG. 6 partially donned on a body and including the sacrificial attachment portion unattached to the attachment region.
Figure 8:
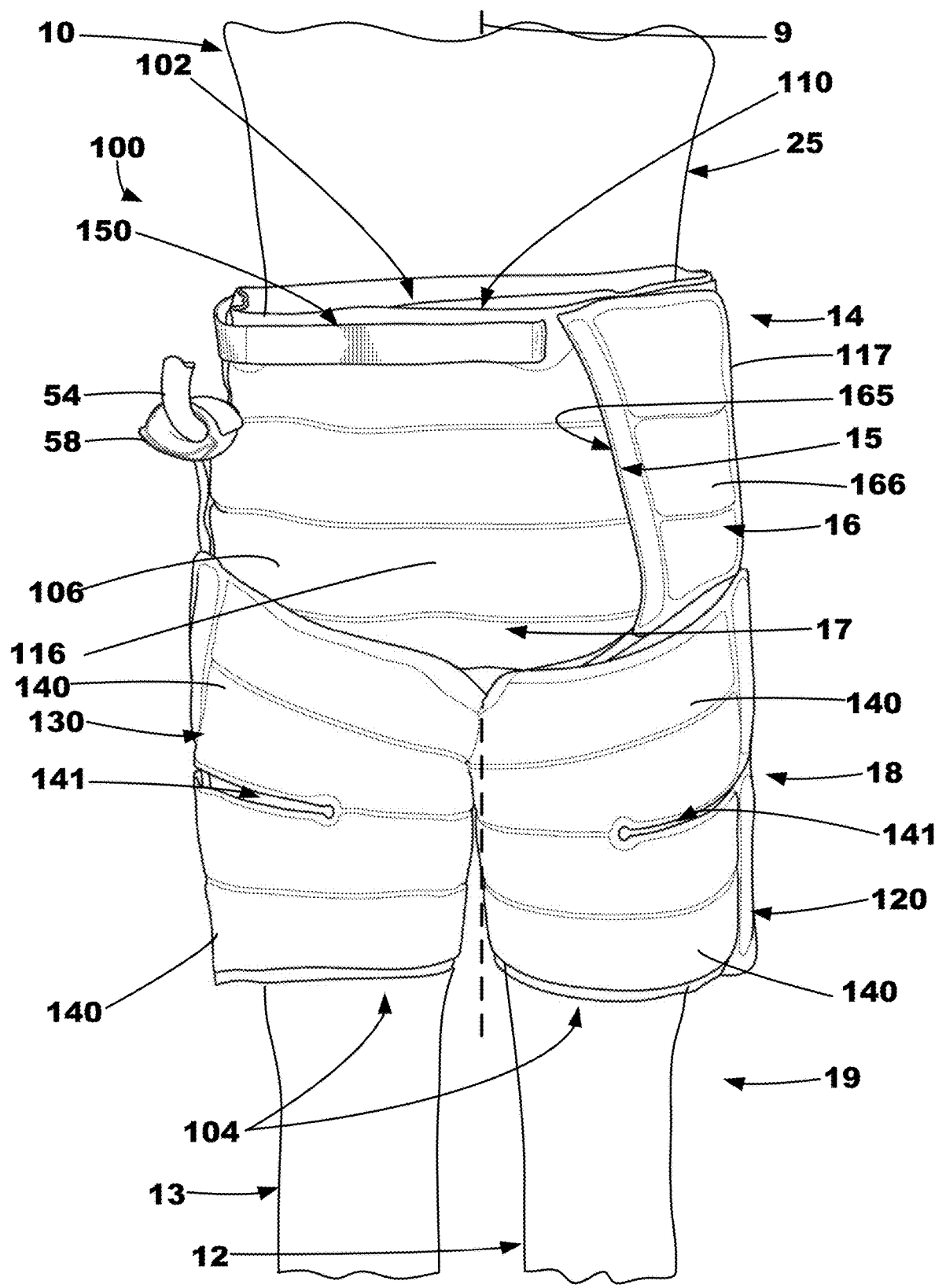
FIG. 8 is a front perspective view of the trunk garment of FIG. 6 fully donned on a body.
Figure 9:
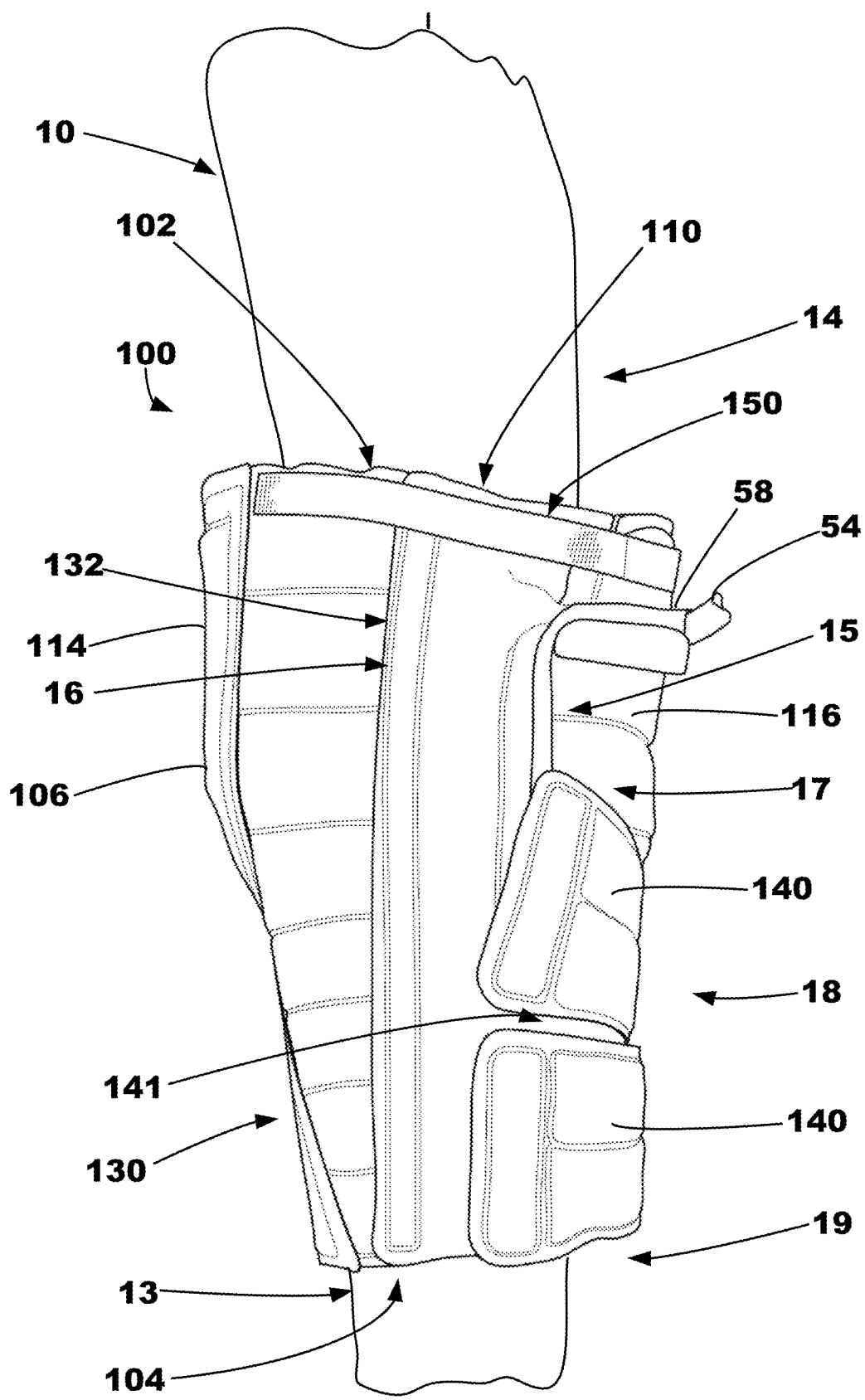
FIG. 9 is a left perspective view of the trunk garment of FIG. 8.
Figure 10:
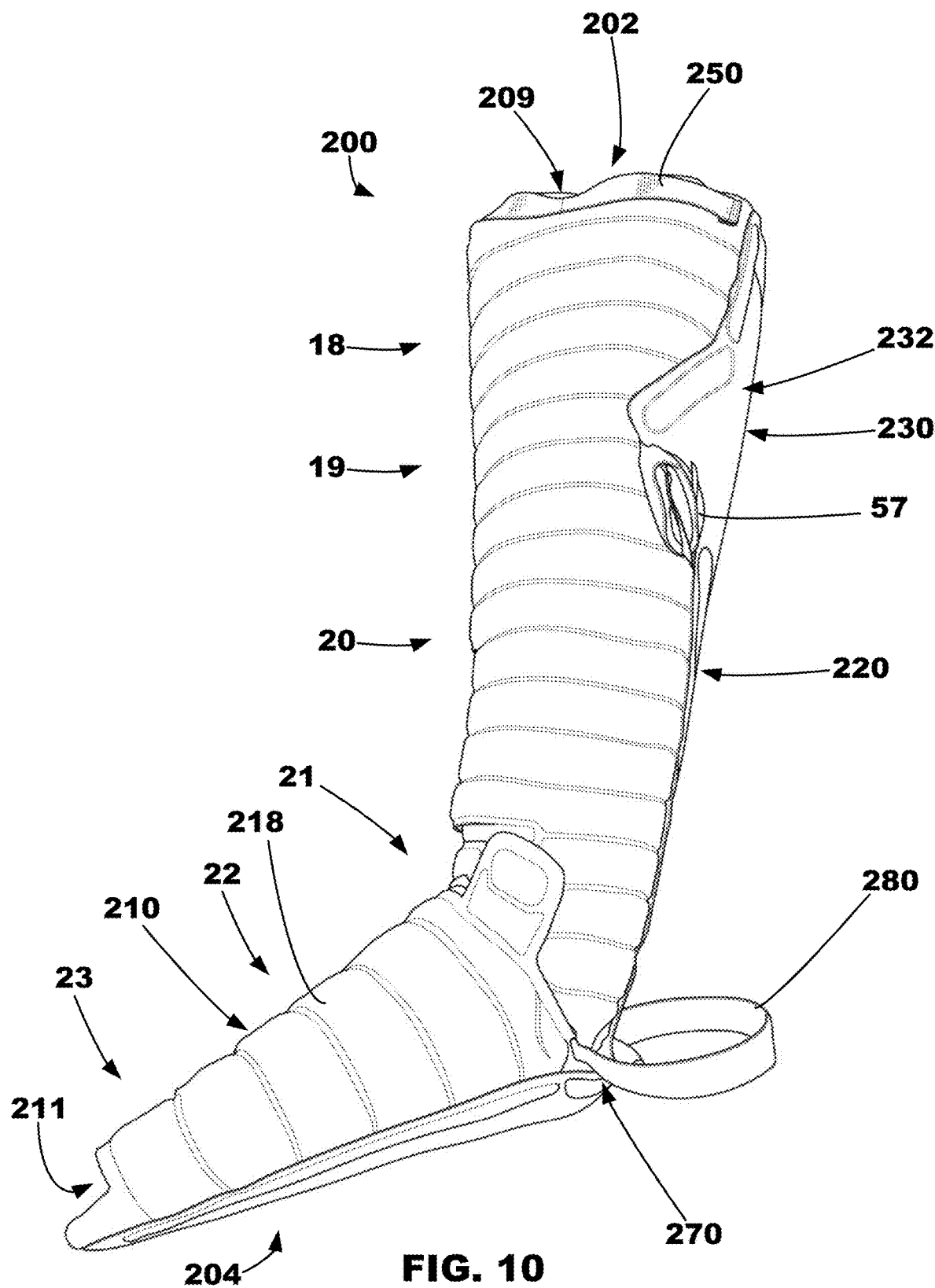
FIG. 10 is a right perspective view of the leg garment of the system of FIG. 1.

To remove the trunk garment 100, the second anterior region 116 may be removed from being coupled to the first anterior region 112 at the trunk attachment area 162. Frequent coupling and uncoupling of the second anterior region 116 from the first anterior region 112 may result, in some instances, in a weakening of the removable coupling defined therebetween. In other words, the more that the first and second anterior regions 112, 116 are attached and unattached, the removable connection, or coupling, apparatus such as a hook-and-loop fastener may lose some of its coupling properties, e.g., due to fatigue, etc. Thus, in one or more embodiments, the second anterior region 116 may be removably coupled to the first anterior region 112 using a sacrificial attachment portion 170 as shown in FIG. 7B. The sacrificial attachment portion 170 may be removably coupled to the first anterior region 112 at the trunk attachment area 162 and may also be removably coupled to the second anterior region 116 thereby coupling the first anterior region 112 to the second anterior region 116. In other words, the sacrificial attachment portion 170 may be described as an intermediate coupling element located between the first anterior region 112 and the second anterior region 116. In one or more embodiments, the removable coupling between the sacrificial attachment portion 170 and the first anterior region 112 is stronger than the removable coupling between the sacrificial attachment portion and the second anterior region 116. In this way, when a user grasps the second anterior portion 116 and moves the second anterior portion 116 away from the first anterior portion 112, the removable coupling between the second anterior portion 116 and the sacrificial attachment portion 170 will release while the removable coupling between the first anterior portion 112 and the sacrificial attachment portion 170 will remain secured. Thus, the sacrificial attachment portion 170 may remain attached to the first anterior portion 112 while the second anterior portion 116 is detached from the sacrificial attachment portion 170. Because the sacrificial attachment portion 170 may not be repeatedly attached and unattached to the first anterior portion 112, the integrity (e.g., the coupling properties) of the surface of the first anterior portion 112 may be maintained (e.g., no fatigue of the surface of the first anterior portion 112 due to the minimal or non-existent attachment and detachment between the first anterior portion 112 and the sacrificial attachment portion 170).

The wraparound portion 110 may define mitt opening 165 to receive a hand of the user to move the wraparound portion 110 about the trunk 12 of the user to, e.g., adjust (e.g., tighten, loosen, reposition, etc.) the wraparound portion 110, and in turn, the trunk garment 100, about the trunk 12 of the user. More specifically, the second anterior region 116 of the wraparound portion 110 may be described as extending from the posterior region 114 and terminating at a mitt end area 117. In other words, the wraparound portion 110 may not extend past the mitt end area 117.

The wraparound portion 110 may include a mitt 166 at the mitt end region 117 defining the mitt opening 165 configured, or designed, to receive a hand of a user to assist the user in donning the trunk garment 100. In one or more embodiments, the mitt opening 165 may be sized to receive more than the fingers of the hand of the user. In one or more embodiments, the mitt opening 165 may be defined by three closed sides and one open side. In other words, the mitt 166 may form a pocket, which may be referred to as the mitt opening 165. Further, in one or more embodiments such as shown in the figures, a closed side of the mitt opening 165 may terminate the mitt end area 117 of the wraparound portion 110. In one or more embodiments, a first portion of the mitt 166 may be part of the second anterior region 116 of the wraparound portion 110 and a second portion of the mitt 166 may be attached, or coupled, (e.g., stitched, adhered, etc.) to the second anterior region 116 of the wraparound portion 110 to create, or provide, the mitt 166 and mitt opening 165 (e.g., attached on three sides to provide one open side). Nonetheless, it is to be understood that the mitt 166 and mitt opening 165, or pocket, may be formed in any manner. For example, the mitt 166, and thus, the mitt opening 165, may be created, or formed, by folding a portion of the wraparound portion 110 back onto itself and coupling the top and bottom edges to form a pocket defining the mitt opening 165.

The mitt 166 as well the mitt opening 165 may be sized and constructed such that the mitt opening 165 is configured to receive more than the fingers, or a portion of the fingers, of a user's hand. In other words, the mitt opening 165 may define a pocket that is larger than a typical-human user's fingers so as to receive a typical human-user's hand or at least a majority of the user's hand. Further, the mitt opening 165 may be described in terms of a user's metacarpophalangeal joints (e.g., the joints between the phalangeal and metacarpal bones). For example, the mitt opening 165 may be configured in size to receive, or hold, the index finger, the middle finger, the ring finger, the pinky, and at least a portion, or region, of a user's hand beyond the metacarpophalangeal joints of the user's hand. In other words, the trunk garment 100 may be described as including an "oven mitt" 166 defining an "oven mitt" pocket 165 that may allow for easy, single-handed trunk garment 100 opening and closing about the waist of the body 10 of the user.

The leg garment 200, which is depicted by itself in FIGS. 10-15, may be generally described as being positionable relative to the body 10 to provide compression therapy to one or more regions of the legs 12, 13 including the feet of the body 10. Although only a single leg garment 200 is depicted as being donned about the left leg 12 of the body 10 of the user, it is to be understood that more than one leg garment 200 may be used by a user at the same time. More specifically, two leg garments 200 may be positionable relative to the body 10 to provide compression therapy thereto such as one leg garment 200 providing compression therapy to the left leg 12 and one leg garment 200 providing compression therapy to the right leg 13.

The leg garment 200 may be described as extending from an upper end region 202 to a lower end region 204 generally along a leg 12 of the body 10. When the leg garment 200 is donned about the body 10, the upper end region 202 may be positioned, or located, in an area proximate the femoral region 18 (e.g., thigh) depending on the size of the leg garment 200 relative the size of the body 10. In one or more embodiments, the leg garment 200 may overlap or be overlapped by a portion of the trunk garment 100 proximate the lower end region 104 such as, e.g., a region of the left upper leg portion 120 or a region of the right upper leg portion 130. For example, the embodiment depicted in FIGS. 1-5 depicts the leg garment 200 donned about the left leg 12 of the body 10 so as to overlap a region, or section, of the left leg portion 120 of the trunk garment 100. More specifically, the leg garment 200 overlaps the left leg portion 120 of the trunk garment 100 such that the upper end region 202 of the leg garment 200 is located approximately between the two thigh straps 140 coupled to the left leg portion 120. In this way, the leg garment 200 appears to overlap two pressure applying regions 101 of the trunk garment 100. It is to be understood that, although the compression garments described herein may be produced in various sizes, the fitment of the various sizes will also be affected by the size of the body 10 that the compression garments are donned thereon. As such, there may be circumstances where the leg garment 200 does not overlap or even contact the trunk garment 100, and there may be circumstances where the leg garment 200 overlaps the trunk garment 100 more than or less than depicted in the embodiment of FIGS. 1-5.

In one or more embodiments, when the leg garment 200 is donned about the left leg 12 of the body 10, the lower end region 204 may be positioned, or located, in an area proximate the pedal, or foot, region 22 as depicted. In other embodiments, the leg garment 200 may not extend as distally as depicted. For example, when the leg garment 200 is donned about the left leg 12 of the body 10, the lower end region 204 may be positioned, or located, in an area proximate the tarsal, or ankle, region 21 or even less distally such as the crural region 20. Thus, it may be described that the leg garment 200 extends from the upper end region 202 to at least a region beyond the patellar, or knee, region 19 such as, for example, the crural region 20, the tarsal region 21, the pedal region 22, and the digital/phalangeal region 23. Additionally, similar to as described herein with respect to the upper end region 202 of the leg garment 200, the positioning of the lower end region 204 of the leg garment 200 may depend on the relative sizing of the leg garment 200 and the body 10 upon which the leg garment is donned.

In one or more embodiments, the leg garment 200 may be configured such that the tubing 55 coupled to the leg garment ports is coupled to and extends from the leg garment 200 between the upper end region 202 and the lower end region 204 as opposed to, e.g., extending from the upper or lower end regions 202, 204, which may be cumbersome and provide weight to undesirable portions of the leg garment causing discomfort. In other words, the tubing 55 may be coupled to and extend from the leg garment 200 in a middle region that is between the lower end region 204 and the upper end region 202.

Figure 14:
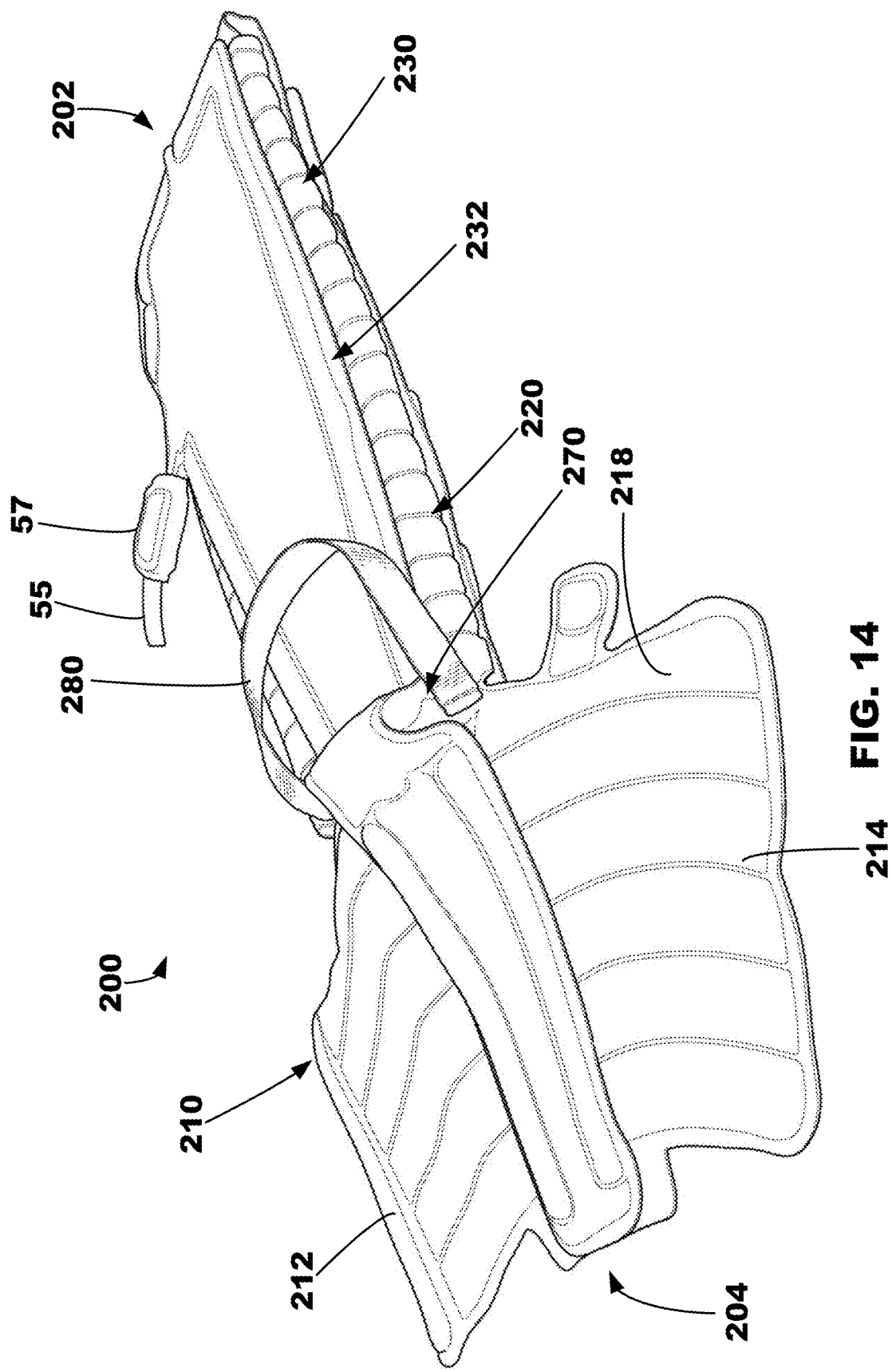
FIG. 14 is an additional rear perspective view of the leg garment of FIG. 10 with the foot garment portion unwrapped.

Further, as shown in FIG. 14 and more specifically, the tubing 55 may be coupled to and extend from the leg garment 200 between the upper end region 202 and the patellar region 19. In other embodiments, the tubing 55 may be coupled to extend from the leg garment 200 between at the patellar region 19 or even more distally than the patellar region 19 such as, e.g., at the crural region 20, at the tarsal region 21, and at the pedal region 22.

In other words, the tubing, or hoses, 55 may exit off the side of the leg garment 200, e.g., near the calf, which may reduce discomfort to users. For example, garments where hoses, or tubing, extend from the end of the foot may add weight to the end of the foot, and thus, may pull the foot into a pronate position, which can be uncomfortable to the user. Thus, tubing, or hoses, 55 exiting from the side of the leg garment 200 as shown and described herein may reduce this discomfort.

The leg garment 200 may further include one or more or a plurality of loop portions 250 coupled to and extending from the upper end region 202. The loop portions, or webbing, 250 may define one or more loops configured to be grasped by a user when donning or removing the leg garment 200. In one or more embodiments, the loop portions 250 may be located substantially all the way around the leg garment 200. In one or more embodiments, the loop portions 250 may only be located in one or more selected areas about the leg garment 200 such as one or more of the anterior side, the posterior side, the left side, and the right side. In at least one embodiment, the loop portions 250 may be woven nylon strapping that is stitched to the upper end region 202 of the leg garment 200.

Figure 11:
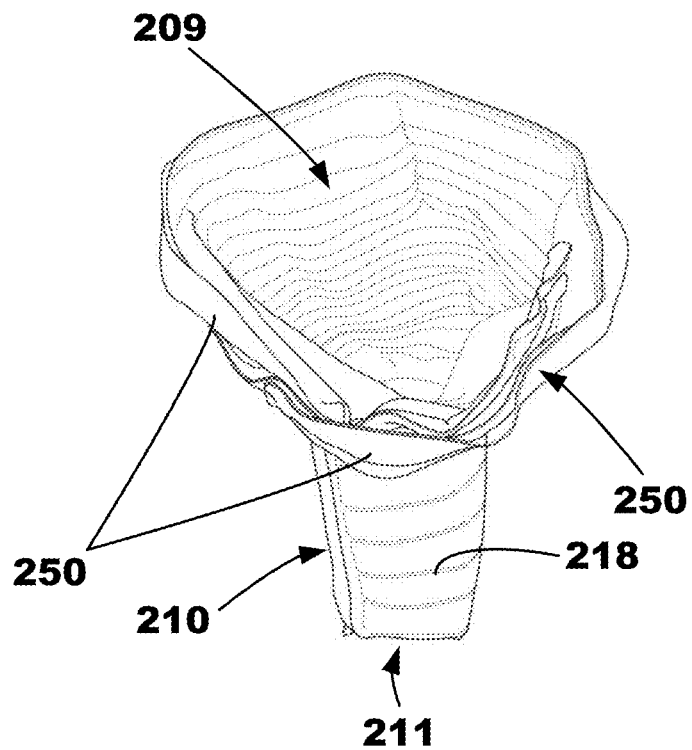
FIG. 11 is a top perspective view of the leg garment of FIG. 10.
Figure 12:
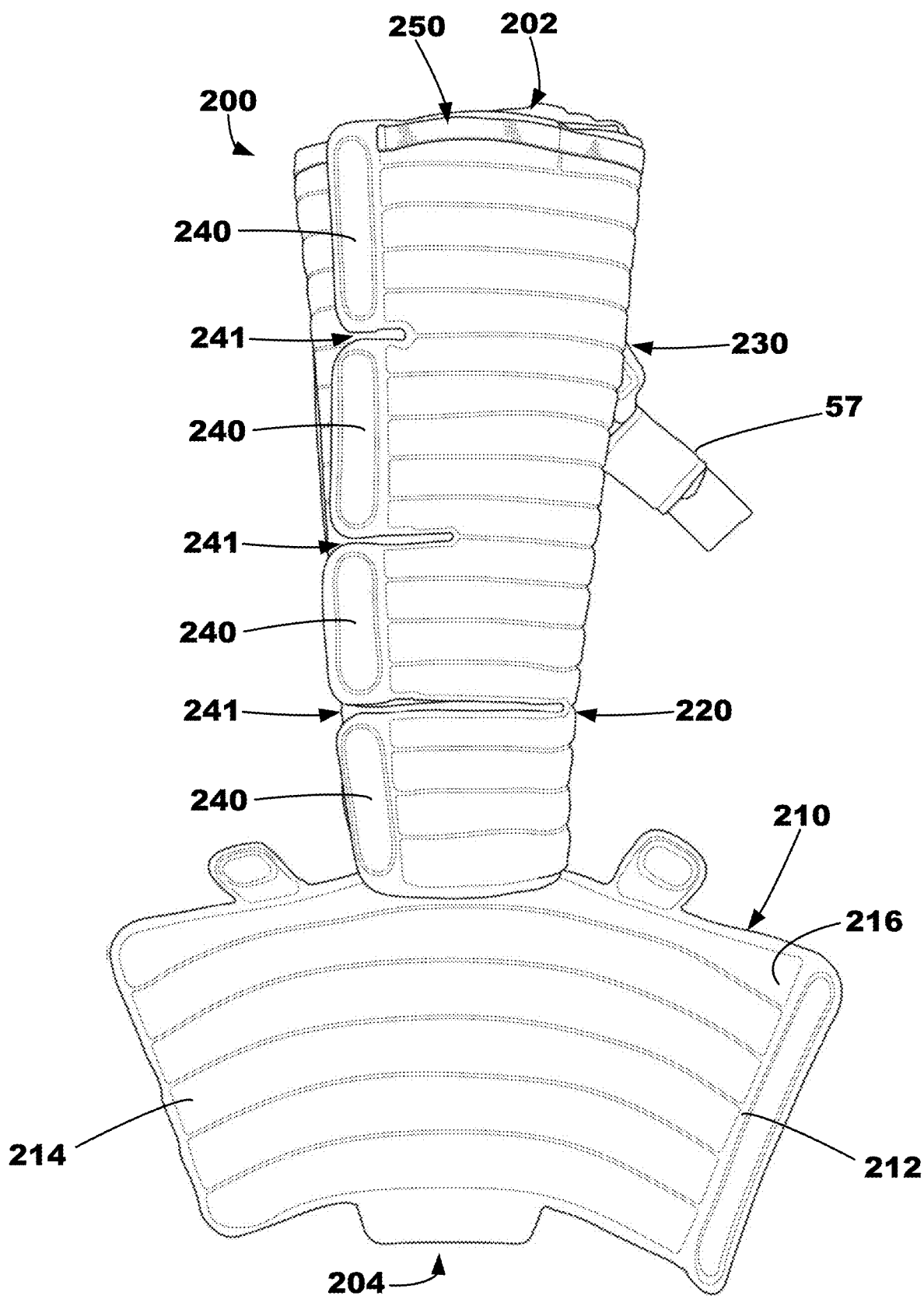
FIG. 12 is a front plan, perspective view of the leg garment of FIG. 10 with the foot garment portion unwrapped.

The leg garment 200 may include foot portion 210 configured to be located proximate user's foot when donned, a calf portion 220 configured to be located proximate user's calf when donned, and thigh portion 230 configured to be located proximate user's thigh when donned. To adjust the size of the leg garment 200 to, for example, achieve a proper fit about a user's leg, the leg garment 200 may include a plurality of adjustable leg straps 240 that are coupled to and extend from one of the calf portion 220 and the thigh portion 230. The plurality of adjustable leg straps 240 may be removably coupled back to one of the calf portion 220 and the thigh portion 230 to form, or define, a leg opening 209 (e.g., as shown in FIG. 11) for receiving at least a portion of the femoral region 18 (e.g., thigh), patellar region 19, and the crural region 20 of the user's leg 12. When the leg garment 200 is donned about the left leg 12, the leg straps 240 may extend across at least an anterior side of the left leg 12 and are configured to be removably coupled to leg attachment areas of the calf and thigh portions 220, 230, which will be further described herein with respect to FIG. 16. The removable coupling between the leg straps 240 and the leg attachment area may be facilitated using any suitable removable connection apparatus such as, e.g., hook-and-loop fasteners. For example, the leg straps 240 may include the "hook" portion of a hook-and-loop fastener while the leg attachment areas may include the "loop" portion of a hook-and-loop fastener. More specifically, the outer surface of the leg garment 200 at the leg attachment areas may be material that may be or may act as the "loop" portion of a hook-and-loop fastener.

The leg straps 240 may be used to adjust the size of the leg opening 209 of the leg garment 200 including the calf and thigh portions 220, 230 to fit about the leg of the user, e.g., at the desired level of fitment, tightness, snugness, etc. In one or more embodiments, the leg straps 240 may be used to adjust the size of the leg opening 209 along the length of the leg garment 200 during the first, or initial, instance that a user uses the leg garment 200, and thereafter, a user may not adjust the leg straps 240 when donning the leg garment 200. Instead, the user may locate, or slip, the user's leg into the leg opening 209 and then pull the leg garment 200 upward (e.g., using the loop portions 250) towards the user's trunk 25 similar to donning a stocking or sock. In this way, the leg portion garment 200 may remain adjusted to the particular sizing that the user desires. Nonetheless, if a user desires to change the fitment, or size, of the leg opening 209, a user may remove the leg straps 240 from being removably coupled to the leg attachment areas, move the leg straps 240 relative to the calf and thigh portions 220, 230 to achieve the desired level of fitment, and then re-couple the leg straps 240 to the leg attachment areas. Further, each of the leg straps 240 may be adjusted one at time or simultaneously.

Although four leg straps 240 are coupled to and extend from the calf and thigh portions 220, 230 as shown, it is to be understood than the exemplary leg garment 200 described herein may include any number of leg straps 240 coupled to and extending from the calf and thigh portions 220, 230. In one or more embodiments, the leg garment 200 may include a plurality of leg straps 240 coupled to and extending from each of the calf and thigh portions 220, 230 such as, e.g., two or more leg straps, three or more leg straps, five or more leg straps, etc. A gap, or a space, 241 may be defined between the leg straps 240 such that, e.g., each of the leg straps 240 may operate somewhat independently (e.g., because of flexibility of the end of the leg straps 240 relative to one another due to the gaps 241) from each other when being used to adjust the size of leg opening 209 of the leg garment 200.

Figure 16:
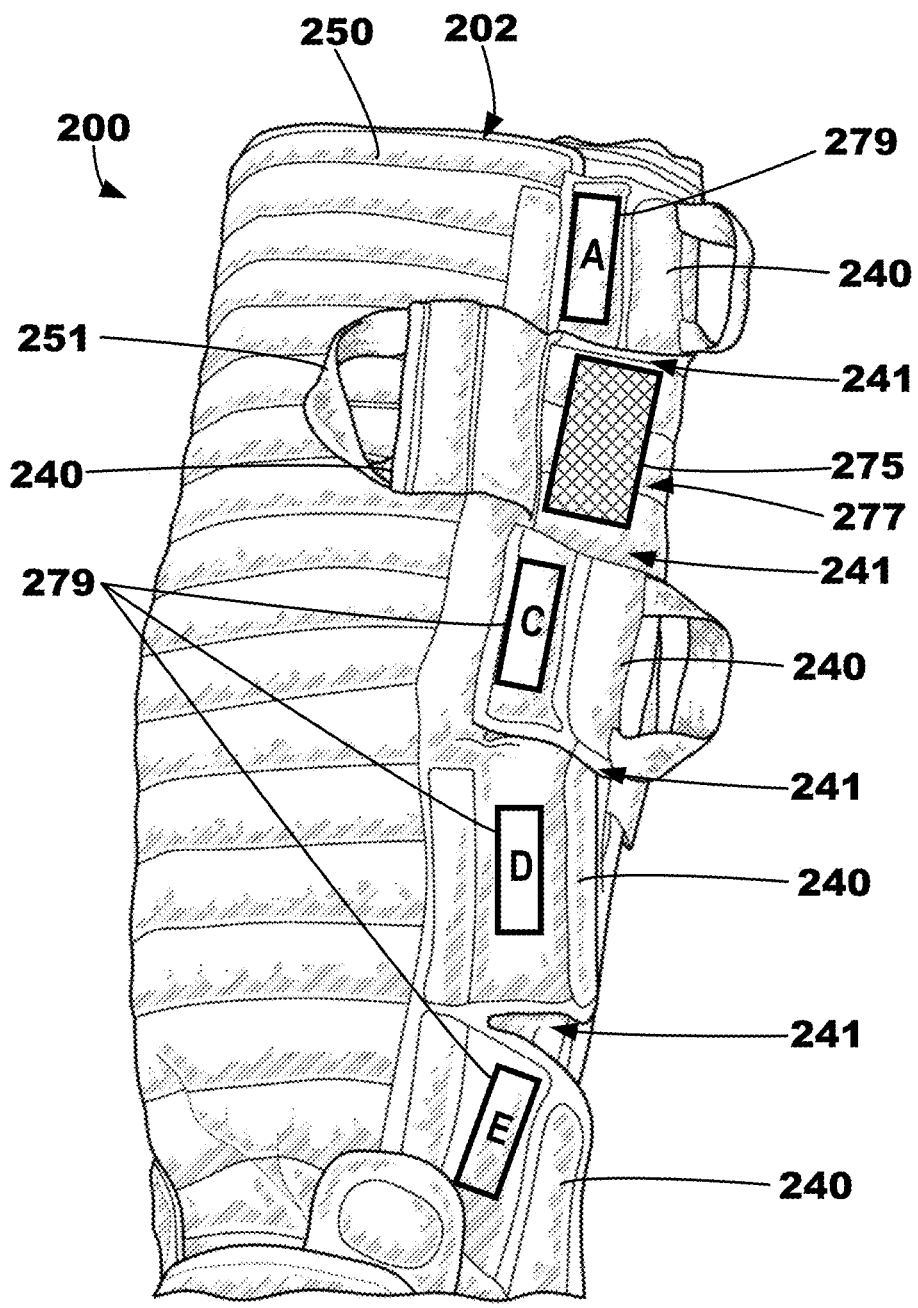
FIG. 16 is a perspective view of a portion of an exemplary leg garment including a sacrificial attachment portion.

The leg garment 200 may also include, or utilize, sacrificial attachment portions with the leg straps 240 for similar reasons as the trunk garment 100. Thus, in one or more embodiments, each leg strap 240 may be removably coupled to a leg attachment area 277 using a sacrificial attachment portion 275 as shown in FIG. 16. The sacrificial attachment portion 275 may be removably coupled to the leg garment 200 at the leg attachment area 277 and may also be removably coupled to the leg strap 240 thereby coupling the leg attachment area 277 to the leg strap 240. In other words, the sacrificial attachment portion 275 may be described as an intermediate coupling element located between the leg attachment area 277 and the leg strap 240. In one or more embodiments, the removable coupling between the sacrificial attachment portion 275 and the leg attachment area 277 is stronger than the removable coupling between the sacrificial attachment portion 275 and the leg strap 240. In this way, when a user grasps the leg strap 240 and moves the leg strap 240 away from the leg attachment area 277, the removable coupling between the leg strap 240 and the sacrificial attachment portion 275 will release while the removable coupling between the leg attachment area 277 and the sacrificial attachment portion 275 will remain secured. Thus, the sacrificial attachment portion 275 may remain attached to the leg attachment area 277 while the leg strap 240 is detached from the sacrificial attachment portion 277.

In one or more embodiments, additional loop elements 251, similar to the loop elements 250, may be coupled to and extend from the one or more leg straps 240 as shown in FIG. 16. The loop elements 251 may define a loop that may be graspable by a user to move and couple the leg straps 240 about the leg garment 200. Further, in one or more embodiments, each of the leg straps 240 of the leg garment 200 may include an identifier 279 such as, e.g., a color, a number, text, etc. that may be used as a training or instructional aid for patients (e.g., to assist the user in donning the leg garment 200). As shown in FIG. 16, the identifiers 279 are letters from the beginning of the alphabet, which may indicate the order in which the leg straps 240 are to be adjusted when adapting, modifying, or tailoring the leg garment 200 about the leg 12, 13 of the body 10 of the user during donning.

Further, the foot portion 210 may also be adjustable to achieve proper fit about a user's foot. The foot portion 210 is shown in an unwrapped configuration in FIGS. 12-13. The foot portion 210 may be described as extending from a first foot end region 212 to a second foot end region 214, and the first and second foot end regions 212, 214 may be removably coupled to each other to define a foot opening 211 (e.g., as shown in FIG. 11) to receive the user's foot. More specifically, the removable coupling between the first foot end region 212 and the second foot end region 214 may be facilitated using any suitable removable connection apparatus such as, e.g., hook-and-loop fasteners. For example, the first foot end region 212 may include the "hook" portion of a hook-and-loop fastener while the second foot end region 214 may include the "loop" portion of a hook-and-loop fastener. Additionally, the foot portion 210 may define an interior surface 216 configured to face the user's foot when the leg garment 200 is donned, and an exterior surface 218 facing opposite the interior surface 216 and away from the user's foot when the leg garment 200 is donned. The exterior surface 218 may be configured such that second foot end region 214 may be removably coupled to any portion of the exterior surface 218 of the foot portion 210, and thus, the exterior surface 218 of the foot portion 210 may act as one half of a hook-and-loop style removable coupling between the first foot end region 212 and the second food end region 214.

Figure 13:
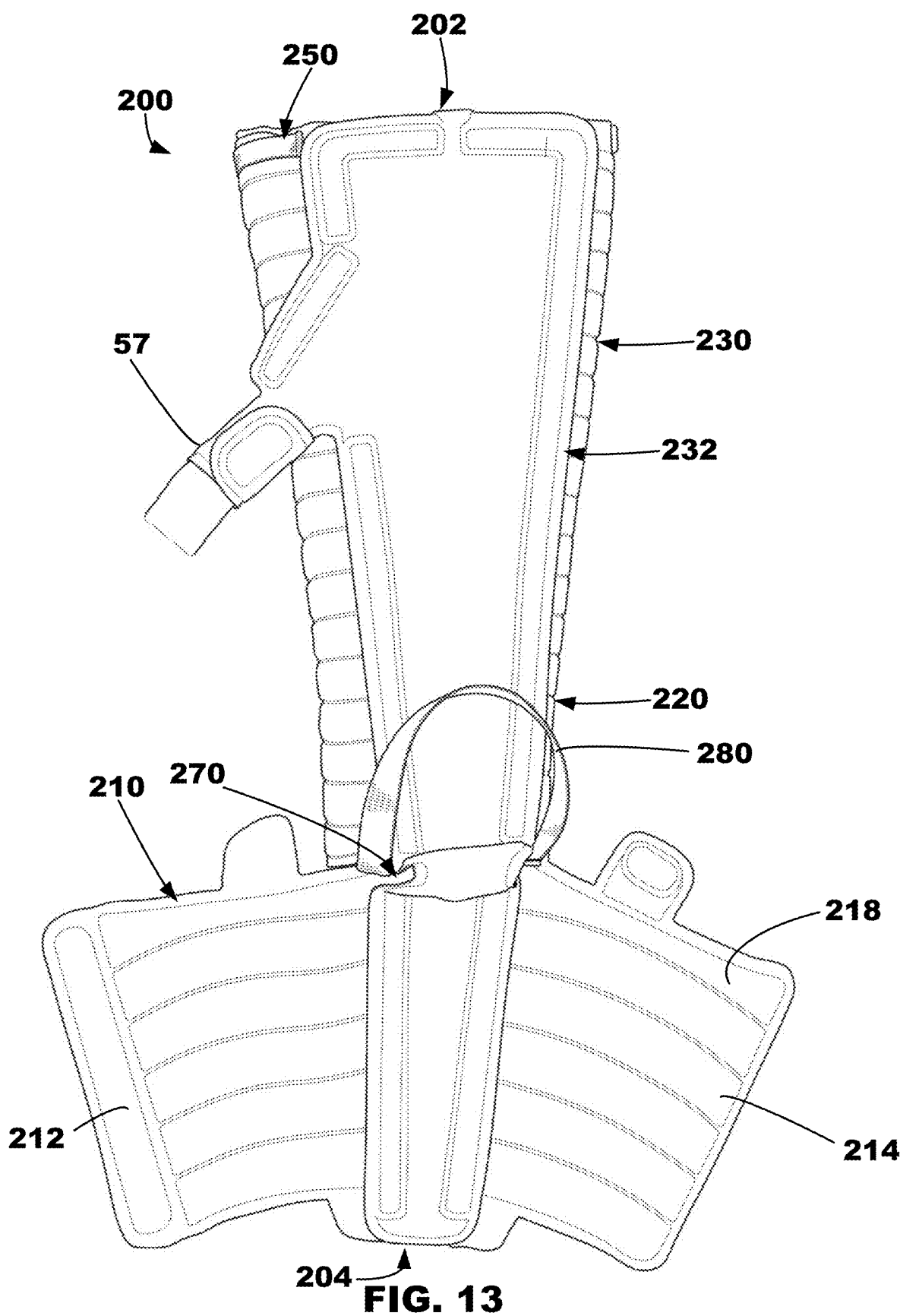
FIG. 13 is a rear plan, perspective view of the leg garment of FIG. 10 with the foot garment portion unwrapped.
Figure 15:
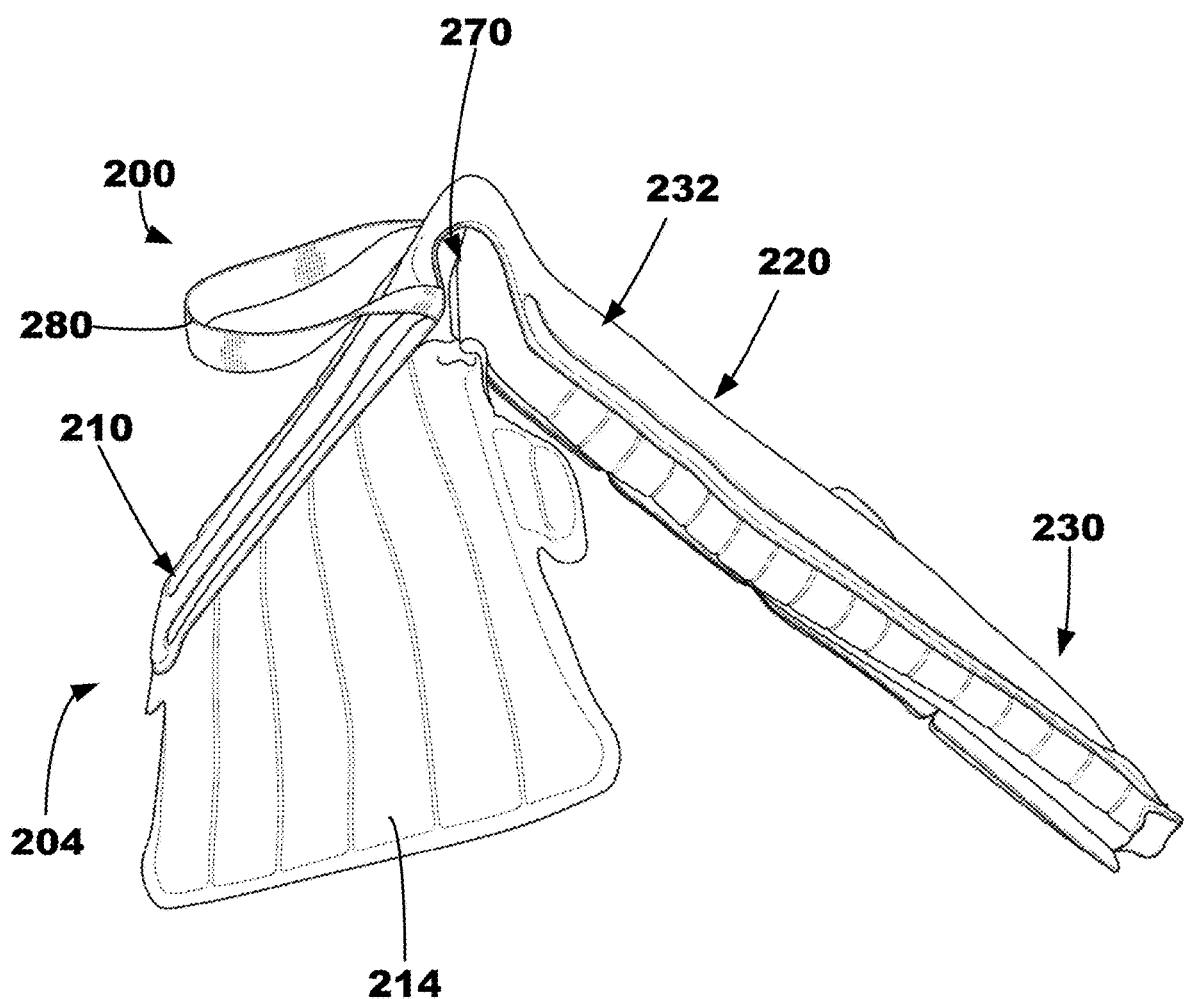
FIG. 15 is a left perspective view of a portion of the leg garment of FIG. 10.

The foot portion 210 may be coupled to the calf portion 220 of the leg garment 200 to facilitate fitment about the tarsal region 21 of the leg 12, 13 of the body 10 of the user. More specifically, the foot portion 210 and the calf portion 220 may be configured to follow the natural anatomical bend from the crural region 20 to the tarsal region 21 and further to the pedal, or foot, region 22 of the user's leg 12, 13. To do so, the leg garment 200 may include a heel element, or heel cup portion, 270 (e.g., as shown in FIGS. 13-15)

configured to receive the heel of the leg 12, 13. The heel element 270 may include material that extends from the calf portion 220 to the foot portion 210 that is configured to be located adjacent the heel of the user's leg 12, 13 when the leg garment 200 is donned. Additionally, the heel element 270 may assist users to orient their foot with respect the leg garment 200. The heel element 270 may be described as effectively defining a cup or depression to receive the heel of the user's leg 12, 13 to effectively position the remainder of the leg garment 200 such as, e.g., the calf portion 220 and the foot portion 210, about the leg 12, 13.

More specifically, as shown in a plan view of an embodiment of a leg garment 200 in FIG. 17, the heel element 270 may include (e.g., be formed by) a center portion 272 that extends between the calf portion 220 and the foot portion 210 and a pair of side cup portions that define the left and right sides of the heel element 270 (e.g., portions that are located on either side of the user's heel when the user's heel is positioned in the leg garment 200 with the heel proximate the heel element 270). Each of the side cup portions may be created, or formed, by coupling (e.g., stitching together, adhering, etc.) a first heel tab portion 229 of the calf portion 220 to a second heel tab portion 219 of the foot portion 210 as indicated by the double-sided dashed lines in FIG. 17. By doing so, the calf portion 220 and the foot portion 210 may be "pulled together" to form, or define, a heel cup centered about the central portion 272 and defined on the left and right sides by the side cup portions (e.g., that were created by joining the first and second heel tab portions 229, 219). Additionally, the formation of the heel element 270 may also position the foot portion 210 to extend at an angle from the remainder of the leg garment 200 so as to fit that natural curvature of a user's leg more effectively. In other words, the leg garment 200 may define a tube that mimics that natural curvature of a user's leg including the curvature from the user's calf to foot or ankle region.

The leg garment 200 may further include strap element 280 coupled to and extending from one or both of the foot portion 210 and the calf portion 220 proximate the tarsal region 21, and more specifically, proximate the heel of the leg 12 when the leg garment 200 is donned about the leg 12. The strap element 280 may form a loop that may be configured to receive a portion of the user's foot on the right leg 13, which is not received, or donned, by the leg garment 200, when removing the leg garment 200 from the user's left leg 12. For example, a user may use their opposing leg to "push off" or hold the leg garment 200 steady while removing their leg from the leg garment 200. For example, a user may stand and place a portion of their opposing foot through a loop created by the strap element 280 and then pull their leg out of the leg opening 209 of the leg garment 200.

Figure 18A:
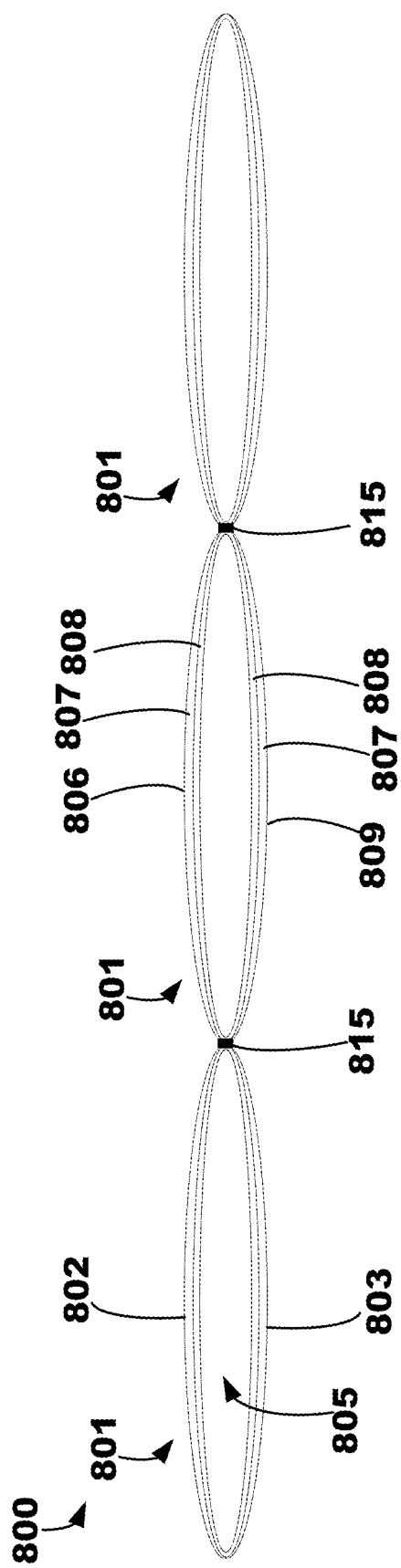
FIG. 18A is a cross-sectional view of one or more chambers or cells (e.g., inflatable chambers or cells) of an exemplary compression garment that may be used with one of the exemplary garments such as shown in FIGS. 1-17.

A cross-section of a portion 800 of an exemplary garment including one or more chambers, or cells, 801 which may be used in providing any of the garments described herein is shown in FIG. 18A. The garment portion 800 may define an exterior surface 802 configured to face the exterior, e.g., away from a user when wearing the garment portion 800, and an opposing interior surface 803 configured to face the interior, e.g., towards a user wearing the garment portion 800. The interior surface 803 may be configured to be positioned closer to the human body than the exterior surface 802 when the garment portion 800 is positioned on the body. As shown, the garment portion 800 defines a plurality of chambers configured and corresponding to pressure applying regions. Each of the chambers 801 defines a volume 805 that may be separated in any way that isolates the volume 805 of a chamber from the volumes of the other chambers 801. For example, the volumes 805 of the chambers 801 may be separated by welds 815, e.g., welds between one or more layers of the garment portion 800 as will be further described herein. The volumes, or cavities, 805 defined by, or in each, of the chambers 801 may be configured to receive a fluid. The fluid may be received from a source (e.g., from pump 53 shown in FIG. 1) to apply pressure at a pressure applying region of the garment to a body portion when garment portion 800 is worn by a user. For example, fluid may be directed to each of the volumes 805 of the chambers 801 in a sequential or non-sequential manner.

Further, each of the various pressure applying regions described herein may include, e.g., one of the one or more chambers 801 or a plurality of the chambers 801. In one or more embodiments, different pressure applying regions described herein may include, e.g., the same one or more chambers, but may, e.g., be positioned at different locations on the garment.

The garment portion 800 may include one or more layers from the exterior surface 802 to the interior surface 803. For example, the exterior facing layer 806, or the layer defining the exterior surface 802, may include one or more fabric materials so as to define a "hook" surface on the exterior surface 802 for coupling to a "loop" surface or material forming, or defining, a "hook-and-loop" fastener. The exterior surface of the exemplary garment portions described herein may be partially or completely defined by a "hook" surface for use in a "hook-and-loop" fastener.

A foam layer 807 may be adjacent the exterior facing layer 807, and then a polymer layer 808 (e.g., polyurethane, polyvinyl, etc.) may be located adjacent the foam layer 807 facing the volume 803 of the chamber 801. The interior side of the garment portion 800 may be similar to the exterior side except that, instead of an exterior facing layer, the foam layer 807 may be adjacent a fabric layer 809 configured to be located adjacent the portions of the body 10.

Figure 18B:
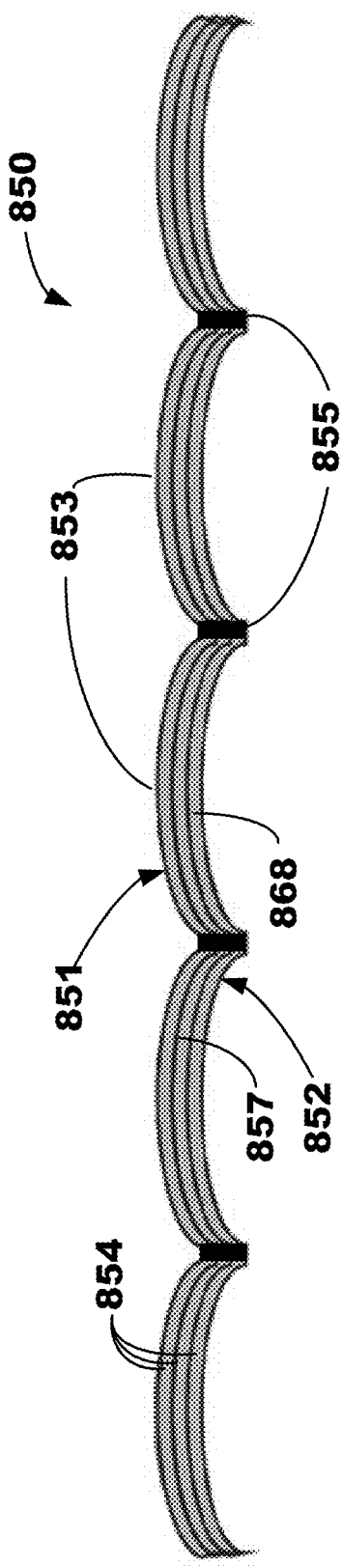
FIG. 18B is a cross-sectional view of one or more cells including actuatable elements (e.g., without inflatable chambers or cells) of an exemplary compression garment that may be used with one of the exemplary garments such as shown in FIGS. 1-17.

A cross-section of another portion 850 of exemplary garment including one or more compression regions 853 which may be used in providing any of the garments described herein is shown in FIG. 18B. The garment portion 850 may define an exterior surface 851 and an opposing interior surface 852. The interior surface 852 may be configured to be positioned closer to the human body than the exterior surface 851 when the garment portion 850 is positioned on the body. The one or more regions 853 may be separated or may not need to be separated from one another. In one embodiment, for example, the one or more regions 853 may be separated by welds 855.

The garment 850 may include one or more layers 854, with at least one of the one or more layers 854 including a compression layer 857. The compression layer 857 may include a variety of suitable components configured to apply pressure. For example, the pressure may be applied through the compression layer by an air or pneumatic system, a hydraulic system, an electro-mechanical system, actuated elements (e.g., an electrical signal may be used to actuate an element within the garment, such as electrically actuatable fibers in the garment, such that the compartment including such fibers applies a pressure to a portion of the body), a cable/lace tensioning system, or any other system that is configured to apply pressure to the portion of the body through the garment portion 850.

In at least one embodiment, the compression layer 857 may be a plurality of actuated elements configured to apply pressure to the portion of the body (e.g., actuatable material, such as nitinol, or any other compressing devices). The compression layer 857 of each of the one or more regions 853 may apply pressure to body portion when the garment portion 850 is worn by a user. For example, pressure may be applied by each of the one or more regions 853 in a sequential or in a continuous manner over the one or more regions 853. Each of the various pressure applying regions described herein may include, e.g., one of the one or more regions 853 or a plurality of the one or more regions 853. In one or more embodiments, different pressure applying regions described herein may include, e.g., the same one or more regions, but may, e.g., be positioned at different locations on the garment portion 850.

The garment portions 850, described in FIG. 18B (which may be used in any of the compression garments and portions thereof described herein), may also be associated with one or more pressure sensors 868 configured to measure pressure applied to the portion of the body by the garment portions 850. The pressure sensors 868 may be located at a variety of positions along the garment portion 850. For example, the pressure sensors 868 may be positioned (e.g., at an equal distance apart or as necessary) along the length of the garment portion 850. The pressure sensors 868 may be located adjacent the one or more of the pressure applying regions or multiple layers 854 of the garment portion 850.

For example, one layer of material may encompass pressure sensors 868 including pressure sensing regions corresponding to the one or more pressure applying regions and/or corresponding to the one or more chambers 801, 853. In one or more embodiments, the pressure sensors 868 may be positioned on a side of the garment portions 800, 850 that may be proximate the portion of the body (e.g., the interior surface 802, 852, etc.). The pressure sensors 868 may be positioned for sensing pressure at, e.g., each pressure applying region, each of the one or more chambers 801, 853, a manifold for multiple chambers, etc.

Pressure sensor apparatus may be implemented for sensing pressure in a plurality of different manners at, e.g., each pressure applying region, each air cell or chamber, a manifold for multiple chambers, etc. The pressure sensor apparatus may be configured to measure pressure in a variety of different ways, e.g., one sensor for each pressure applying region, a single sensor for all of the pressure applying regions, etc. Additionally, the controller may be configured to control the pressure applied to the portion of the body based on the measured pressure. For example, pressure sensing apparatus may take the form of using pressure sensors within the garment as described in U.S. Pat. No. 9,027,408 entitled "Elastomeric Particle Having An Electrically Conducting Surface, A Pressure Sensor Comprising Said Particles, A Method For Producing Said Sensor And A Sensor System Comprising Said Sensors," or a pump or control apparatus may be provided with pressure sensing functionality (e.g., measuring pressures of air in chambers as part of the pump apparatus) such as described in U.S. Pat. No. 7,947,003 entitled "Pressurized Medical Device," all of which are incorporated by reference herein.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Particular materials and dimensions thereof recited in the disclosed examples, as well as other conditions and details, should not be construed to unduly limit this disclosure. Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed:

1. A compression garment system comprising:
    a trunk garment to be donned about a trunk of a user adapted to apply compression to the trunk and at least a portion of both legs of the user, wherein the trunk garment comprises one or more trunk pressure applying regions controllable to apply pressure to a portion of the trunk and at least a portion of both legs of the user, wherein the trunk garment further comprises a wraparound portion extending from a first anterior end region to a second anterior end region and configured to be wrapped about the user's trunk, wherein the second anterior region is removably couplable to the first anterior region at a trunk attachment area to don the trunk garment about the trunk of the user, wherein the trunk garment extends from an upper end region to a lower end region, and wherein the lower end region further comprises:
        a left upper leg portion configured to wrapped about at least a portion of left leg of the user to apply compression to at least a portion of the left leg of the user when the trunk garment is donned by the user; and
        a right upper leg portion configured to wrapped about at least a portion of right leg of the user to apply compression to at least a portion of the right leg of the user when the trunk garment is donned by the user,
    wherein each of the left and right upper leg portions extends from the upper end region beyond a groin region towards a patellar region of the user when the trunk garment is donned by the user;
    a leg garment to be donned about a right or left leg of the user adapted to apply compression to the leg, wherein the leg garment comprises one or more leg pressure applying regions controllable to apply pressure to at least a portion of the leg;
    tubing operably coupled to the one or more trunk pressure applying regions to transmit fluid to the one or more trunk pressure applying regions, wherein the tubing extends from the trunk garment and the tubing is coupled to, extends from, and exits the trunk garment at a single location between the upper end region and the lower end region; and
    a strain relief portion comprising a wraparound element and a tongue element, wherein a first end of the tongue element is fixed to and extends from the trunk garment and a second end of the tongue element is removably coupled to the wraparound element, and wherein the wraparound element is configured to wrap around the tubing to secure the tubing to the tongue element by attaching and wrapping an end portion of the wraparound element to and around the tubing and the second end of the tongue element so that movement of the tubing will move both the wraparound element and the tongue element, and wherein the strain relief portion is adapted to relieve strain from a coupling area where the tubing is coupled to the one or more trunk pressure applying regions.

2. The system of claim 1, wherein the trunk garment defines:
a right upper leg opening adapted to receive at least portion of a femoral region of the right leg of the user; and
a left upper leg opening adapted to receive at least portion of the femoral region of the left leg of the user, wherein the trunk garment applies compression to at least portion of the femoral region of both of the right and left legs of the user when the trunk garment is donned by the user.

3. The system of claim 1, wherein the upper end region is locatable proximate an abdominal region of the user, and wherein the lower end region is locatable proximate a femoral region of both of the right and left legs of the user.

4. The system of claim 3, wherein the trunk garment further comprises one or more loop portions proximate the upper end region to be grasped by a user when donning the trunk garment to assist in donning the trunk garment.

5. The system of claim 1, wherein the one or more trunk pressure applying regions are concentrically positioned about the trunk of the user such that each of the one or more trunk pressure applying regions substantially lies in a plane perpendicular to an axis extending substantially along the spine of the user when the trunk garment is donned by the user.

6. The system of claim 1, wherein the wraparound portion of the trunk garment defines a mitt opening proximate the second anterior end region to adapted receive a hand of the user to move the wraparound portion about the trunk of the user.

7. The system of claim 1, wherein the trunk garment comprises a plurality of thigh strap portions for each of the user's legs adapted to extend across an anterior side of the user's thighs and are removably couplable to a thigh attachment region of the trunk garment to don the trunk garment about the thighs of the user, wherein the plurality of thigh strap portions define a gap between at least two thigh strap portions.

8. The system of claim 1, wherein the leg garment extends from an upper end region to a lower end region, wherein the upper end region of the leg garment is located proximate at least a femoral region of the leg of the user when the leg garment is donned and the lower end region of the leg garment is located proximate one or more of a crural region, a tarsal region, a pedal region, and a digital/phalangeal region of the leg of the user when the leg garment is donned.

9. The system of claim 1, wherein the system further comprises a controller to control pressure applied by at least one of the one or more trunk pressure applying regions and the one or more leg pressure applying regions to move lymph from at least one of the trunk and the leg.

10. The system of claim 1, wherein the leg garment extends from an upper end region to a lower end region, wherein the upper end region of the leg garment is located proximate at least a femoral region of the leg of the user when the leg garment is donned and the lower end region of the leg garment is located proximate one or more of a crural region, a tarsal region, a pedal region, and a digital/phalangeal region of the leg of the user when the leg garment is donned,
wherein the leg garment comprises a strap element adapted to receive a portion of the foot of the other leg of the user to assist in removing the leg garment from the user's leg, wherein the strap element is located closer to the lower end region of the leg garment than the upper end region of the leg garment.

11. The system of claim 1, wherein each of the left and right upper leg portions extends a same length from the upper end region of the trunk garment to the lower end region of the trunk garment.

12. The system of claim 1, wherein the upper end region of the trunk garment is locatable proximate an abdominal region of the user, and wherein each of the left and right upper leg portions extend from the upper end region at least to a point,
wherein the point is locatable proximate at least an area positioned about halfway between a pelvic region and the patellar region when the trunk garment is donned by the user.

13. A compression garment system comprising:
a trunk garment to be donned about a trunk of a user adapted to apply compression to the trunk and at least a portion of both legs of the user, wherein the trunk garment comprises one or more trunk pressure applying regions controllable to apply pressure to a portion of the trunk and at least a portion of both legs of the user, wherein the one or more trunk pressure applying regions are concentrically positioned about the trunk of the user such that each of the one or more trunk pressure applying regions substantially lies in a plane perpendicular to an axis extending substantially along the spine of the user when the trunk garment is donned by the user;
tubing operably coupled to the one or more trunk pressure applying regions to transmit fluid to the one or more trunk pressure applying regions; and
a strain relief portion comprising a tongue element and a wraparound element, wherein a first end of the tongue element is fixed to and extends from the trunk garment and a second end of the tongue element is removably coupled to the wraparound element, and wherein the wraparound element is configured to wrap around the tubing to secure the tubing to the tongue element by attaching and wrapping an end portion of the wraparound element to and around the tubing and the second end of the tongue element, and wherein the strain relief portion is adapted to relieve strain from a coupling area where the tubing is coupled to the one or more trunk pressure applying regions.

14. The system of claim 13, wherein the trunk garment defines:
a right upper leg opening adapted to receive at least portion of a femoral region of the right leg of the user; and
a left upper leg opening adapted to receive at least portion of a femoral region of the left leg of the user, wherein the trunk garment applies compression to at least portion of the femoral region of both of the right and left legs of the user.

15. The system of claim 13, wherein the trunk garment extends from at least an upper end region locatable proximate an abdominal region of the user to at least a lower end region locatable proximate a femoral region of both of the right and left legs of the user.

16. The system of claim 15, wherein the trunk garment further comprises one or more loop portions proximate the upper end region to be grasped by a user when donning the trunk garment to assist in donning the trunk garment.

17. The system of claim 13, wherein the trunk garment comprises a wraparound portion extending from a first anterior end region to a second anterior end region and configured to be wrapped about the user's trunk, wherein the second anterior region is removably couplable to the first anterior region at a trunk attachment area to don the trunk garment about the trunk of the user.

18. The system of claim 17, wherein the wraparound portion of the trunk garment defines a mitt opening proximate the second anterior end region adapted to receive a hand of the user to move the wraparound portion about the trunk of the user.

19. The system of claim 17, wherein the trunk garment further comprises a sacrificial attachment portion removably coupled to the first and second anterior end regions, wherein the removable coupling between the sacrificial attachment portion and the first anterior end region is stronger than the removable coupling between the sacrificial attachment portion and the second anterior end region.

20. The system of claim 13, wherein the trunk garment comprises a plurality of thigh strap portions for each of the user's legs adapted to extend across an anterior side of the user's thighs and are removably couplable to a thigh attachment region of the trunk garment adapted to don the trunk garment about the thighs of the user, wherein the plurality of thigh strap portions define a gap between at least two thigh strap portions.

21. The system of claim 13, wherein the system further comprises a controller to control pressure applied by at least one of the one or more trunk pressure applying regions to move lymph from the trunk.

22. A compression garment system comprising:
a leg garment to donned about a right or left leg of a user adapted to apply compression to the leg, wherein the leg garment comprises one or more leg pressure applying regions controllable to apply pressure to at least a portion of the leg, wherein each of the one or more leg pressure applying regions comprises one or more of a plurality of chambers, wherein the leg garment extends from an upper end region to a lower end region, wherein the upper end region is located proximate at least a femoral region of the leg of the user when the leg garment is donned and the lower end region is located proximate one or more of a crural region, a tarsal region, a pedal region, and a digital/phalangeal region of the leg of the user when the leg garment is donned;
tubing comprising a plurality of ends, wherein the plurality of ends are operably coupled to a respective plurality of garment ports, wherein the plurality of garment ports are respectively coupled to the plurality of chambers of the one or more leg pressure applying regions, wherein the tubing transmits fluid to the plurality of chambers, and wherein a portion of the tubing is coupled to, extends from, and exits the leg garment at a single location between the upper end region and the lower end region; and
a strain relief portion comprising a wraparound element and a tongue element, the tongue element is fixed to and extending from the leg garment at a first end of the tongue element and removably coupled to the wraparound element at a second end of the tongue element, the wraparound element is configured to wrap around the tubing to secure the tubing to the tongue element by attaching and wrapping an end portion of the wraparound element to and around the second end of the tongue element so that movement of the tubing will move both the wraparound element and the tongue element, wherein the strain relief portion is adapted to relieve strain from a coupling area where the tubing is coupled to the one or more leg pressure applying regions.

23. The system of claim 22, wherein the leg garment comprises one or more loop portions proximate the upper end region of the leg garment to be grasped by a user when donning the leg garment to assist in donning the leg garment.

24. The system of claim 22, wherein the leg garment comprises:
a plurality of leg strap portions adapted to extend across at least a portion of the user's leg that are removably couplable to a leg attachment area of the leg garment to don the leg garment about the leg of the user; and
at least one loop portion coupled to at least one leg strap portion to be grasped by a user when donning the leg garment.

25. The system of claim 24, wherein the at least one loop portion comprises a plurality of loop portions, wherein each of the plurality of loop portions comprises an identifier to distinguish each loop portion from each other.

26. The system of claim 22, wherein the leg garment comprises:
a plurality of leg strap portions, each of the plurality of leg strap portions extending across at least a portion of the user's leg and removably couplable to a leg attachment area of the leg garment to don the leg garment about the leg of the user; and
a plurality of sacrificial attachment portions, each of the plurality of sacrificial attachment portions corresponding to a different leg strap portion of the plurality of leg strap portions, wherein the sacrificial attachment portion is removably coupled to the leg garment at the leg attachment area, wherein each of the plurality of leg strap portions is removably couplable to the corresponding the sacrificial attachment portion, wherein the removable coupling between the plurality of sacrificial attachment portions and the leg garment is stronger than the removable coupling between the plurality of sacrificial attachment portions and the plurality of leg strap portions.

27. The system of claim 22, wherein the leg garment further comprises:
a calf garment portion to be donned about the crural region of the leg of the user adapted to apply compression to the crural region, wherein the leg pressure applying regions of the calf garment portion are controllable to apply pressure to a portion of the crural region of the leg of the user; and
a foot garment portion to be donned about the pedal region of the leg of the user adapted to apply compression to the pedal region, wherein the leg pressure applying regions of the foot garment portion are controllable to apply pressure to a portion of the pedal region of the leg of the user; and
a heel element coupling the calf garment portion to the foot garment portion adapted to receive the heel of the leg of the user.

28. The system of claim 27, wherein the heel element defines a curvature to follow the curvature of the tarsal region of the leg of the user adapted to receive the heel of the leg of the user and to provide curvature of the leg garment from the crural region to the pedal region of the leg of the user when the leg garment is donned.

29. The system of claim 22, wherein the leg garment comprises a strap element adapted to receive a portion of the foot of the other leg of the user to assist in removing the leg garment from the user's leg, wherein the strap element is located closer to the lower end region than the upper end region.

30. The system of claim 22, wherein the system further comprises a controller to control pressure applied by at least one of the one or more leg pressure applying regions to move lymph from the leg.

\* \* \* \* \*